US012239702B2

(12) United States Patent
Mogler et al.

(10) Patent No.: US 12,239,702 B2
(45) Date of Patent: Mar. 4, 2025

(54) VACCINATION WITH REPLICON PARTICLES AND OIL ADJUVANT

(71) Applicant: Intervet Inc., Madison, NJ (US)

(72) Inventors: Mark A. Mogler, Ames, IA (US); Erin Strait, Spring Hill, KS (US); Ruud Philip Antoon Maria Segers, Boxmeer (NL)

(73) Assignee: INTERVET INC., Rahway, NJ (US)

( * ) Notice: Subject to any disclaimer, the term of this patent is extended or adjusted under 35 U.S.C. 154(b) by 0 days.

(21) Appl. No.: 16/769,329

(22) PCT Filed: Dec. 3, 2018

(86) PCT No.: PCT/EP2018/083297
§ 371 (c)(1),
(2) Date: Jun. 3, 2020

(87) PCT Pub. No.: WO2019/110481
PCT Pub. Date: Jun. 13, 2019

(65) Prior Publication Data

US 2020/0323975 A1 Oct. 15, 2020

Related U.S. Application Data

(60) Provisional application No. 62/607,101, filed on Dec. 18, 2017, provisional application No. 62/594,342, filed on Dec. 4, 2017.

(51) Int. Cl.

| | |
|---|---|
| ***A61K 39/193*** | (2006.01) |
| ***A61K 9/00*** | (2006.01) |
| ***A61K 9/107*** | (2006.01) |
| ***A61K 39/00*** | (2006.01) |
| ***A61K 47/26*** | (2006.01) |

(52) U.S. Cl.
CPC .......... *A61K 39/193* (2013.01); *A61K 9/1075* (2013.01); *A61K 47/26* (2013.01); *A61K 9/0021* (2013.01); *A61K 2039/53* (2013.01); *A61K 2039/55566* (2013.01)

(58) Field of Classification Search
None
See application file for complete search history.

(56) References Cited

U.S. PATENT DOCUMENTS

| | | | | |
|---|---|---|---|---|
| 7,561,972 | B1 | 7/2009 | Welch et al. | |
| 7,561,973 | B1 | 7/2009 | Welch et al. | |
| 7,805,252 | B2 | 9/2010 | Gustafsson et al. | |
| 8,126,653 | B2 | 2/2012 | Welch et al. | |
| 8,425,922 | B2 * | 4/2013 | Vajdy | A61K 39/21 424/283.1 |
| 8,460,913 | B2 | 6/2013 | Kamrud et al. | |
| 9,441,247 | B2 | 9/2016 | Rayner et al. | |
| 2011/0300205 | A1 * | 12/2011 | Geall | A61K 39/00 424/490 |
| 2012/0237543 | A1 | 9/2012 | Hayes et al. | |

FOREIGN PATENT DOCUMENTS

| | | | |
|---|---|---|---|
| CN | 1798760 | A | 7/2006 |
| CN | 102348466 | A | 2/2012 |
| CN | 103154737 | B | 7/2015 |
| EA | 020962 | B1 | 3/2015 |
| EP | 0382271 | A1 | 8/1990 |
| EP | 2471926 | A2 | 7/2012 |
| EP | 2471926 | A3 | 7/2012 |
| JP | 11269093 | A | 10/1999 |
| JP | 2004516333 | A | 6/2004 |
| JP | 2013531680 | A | 8/2013 |
| JP | 2014522840 | A | 9/2014 |
| RU | 2580299 | C2 | 4/2016 |
| TW | 201300537 | A | 1/2013 |
| WO | 2002053181 | A1 | 7/2002 |
| WO | 2005007689 | A1 | 1/2005 |
| WO | 2009144088 | A2 | 12/2009 |
| WO | 2011008548 | A1 | 1/2011 |
| WO | 2011049677 | A1 | 4/2011 |
| WO | 2012006380 | A2 | 1/2012 |
| WO | 2012025612 | A1 | 3/2012 |
| WO | 2013006834 | A1 | 1/2013 |
| WO | 2013131565 | A1 | 9/2013 |
| WO | 2013152086 | A1 | 10/2013 |
| WO | 2014005958 | A1 | 1/2014 |
| WO | 2016038197 | A1 | 3/2016 |
| WO | 2017162741 | A1 | 9/2017 |
| WO | 2018115435 | A1 | 6/2018 |

OTHER PUBLICATIONS

Allison AC. Squalene and squalane emulsions as adjuvants. Methods. Sep. 1999;19(1):87-93. doi: 10.1006/meth.1999.0832. PMID: 10525443. (Year: 1999).*
Anderson, Tavis K. et al., Population dynamics of cocirculating swine influenza A viruses in the United States from 2009 to 2012, Influenza and Other Respiratory Viruses, 2013, 42-51, 7 (Suppl. 4).
Bredenbeek, Peter J. et al., Sindbis Virus Expression Vectors: Packaging of RNA Replicons by Using Defective Helper RNAs, Journal of Virology, 1993, 6439-6446, 67(11).
Davis, NL et al., Alphavirus replicon particles as candidate HIV vaccines, IUBMB Life, 2002, pp. 209-211, 53.
International Search Report for PCT/EP2018/083297 mailed on Feb. 20, 2019, 13 pages.
Kamrud, K.I. et al., Development and characterization of promoterless helper RNAs for the production of alphavirus replicon particle, Journal of General Virology, 2010, 1723-1727, 91(Pt 7).

(Continued)

*Primary Examiner* — Michelle S Horning
(74) *Attorney, Agent, or Firm* — JONES DAY

(57) ABSTRACT

The present invention relates to vaccination against animal pathogens using alphavirus-replicon RNA particles and oil adjuvants. To a vaccine, and a kit of parts comprising the replicon particles and the oil adjuvant. Also to methods and uses of making and using the vaccine and the components of the kit.

19 Claims, 5 Drawing Sheets

Specification includes a Sequence Listing.

(56) References Cited

OTHER PUBLICATIONS

Liljestrom, P. et al., A new generation of animal cell expression vectors based on the semliki forest virus replicon, Biotechnology, 1991, pp. 1356-1361, 9.
Lundstrom, Kenneth, Alphavirus-Based Vaccines, Viruses, 2014, 2392-2415, 6.
Polo, J.M. et al., Alphavirus DNA and particle replicons for vaccines and gene therapy, Dev. Biol., 2000, 181-185, 104.
Pushko, Peter et al., Replicon-Helper Systems from Attenuated Venezuelan Equine Encephalitis Virus: Expression of Heterologous Genes in Vitro and Immunization against Heterologous Pathogens in Vivo, Virology, 1997, 389-401, 239.
Sandbulte, Matthew R. et al., Analyzing Swine Sera for Functional Antibody Titers Against Influenza A Neuraminidase Proteins Using an Enzyme-Linked Lectin Assay (ELLA), Methods in Molecular Biology, 2014, 337-345, 1161.
Vajdy, Michael et al., Mucosal adjuvants and delivery systems for protein-, DNA- and RNA-based vaccines, Immunology and Cell Biology, 2004, 617-627, 82.
Vander Veen, RL et al, Alphavirus replicon vaccines, Animal Health Research Reviews, 2012, 1-9, vol. 13, No. 1.
A. Franchini, Vitamin E in viral inactivated vaccines, Poult. Sci, Apr. 1994, pp. 666-671, vol. 74 , No. 4.
Wanasawaeng, W., et al., Development of inactivated Newcastle disease vaccine using palm oil as an adjuvant, The Thai Journal of Veterinary Medicine, 2009, 9-16, 39.
Eggen et al., 2010, "One-dose vaccination against M. hyo and PCV2," Pig Progress, Jun. 8, 2010 [online] [retrieved on Jun. 18, 2024]. Retrieved from the Internet :<URL: https://www.pigprogress.net/health-nutrition/one-dose-vaccination-against-m-hyo-and-pcv2/> (4 pages).
Karlsson et al., 2017, "Increased humoral immunity by DNA vaccination using an α-tocopherol-based adjuvant," Hum. Vaccin. Immunother., 13(8):1823-1830.
Schultz-Cherry et al., 2000, "Influenza virus (A/HK/156/97) hemagglutinin expressed by an alphavirus replicon system protects chickens against lethal infection with Hong Kong-origin H5N1 viruses," Virology, 278(1):55-59.

* cited by examiner

SEQUENCE LISTING

<160> NUMBER OF SEQ ID NOS: 2

<210> SEQ ID NO 1
<211> LENGTH: 13
<212> TYPE: DNA
<213> ORGANISM: Artificial Sequence
<220> FEATURE:
<223> OTHER INFORMATION: primer

<400> SEQUENCE: 1
ggcgcgccgc acc 13

<210> SEQ ID NO 2
<211> LENGTH: 8
<212> TYPE: DNA
<213> ORGANISM: Artificial Sequence
<220> FEATURE:
<223> OTHER INFORMATION: 3' flanking sequence

<400> SEQUENCE: 2 ttaattaa 8

VACCINATION WITH REPLICON PARTICLES AND OIL ADJUVANT

CROSS-REFERENCE TO RELATED APPLICATIONS

This application is a national stage entry under 35 U.S.C. § 371 of PCT/EP2018/083297, filed on Dec. 3, 2018, which claims priority to U.S. Ser. No. 62/594,342, filed on Dec. 4, 2017 and U.S. Ser. No. 62/607,101, filed on Dec. 18, 2017, the content of PCT/EP2018/083297 is hereby incorporated by reference in its entirety.

SEQUENCE LISTING

This application incorporates by reference in its entirety the Computer Readable Form (CRF) of a Substitute Sequence Listing in ASCII text format submitted via Patent Center. The Substitute Sequence Listing text file submitted via Patent Center is entitled "14463-242-999 SUB SEQ LISTING.txt," was created on Sep. 30, 2024, and is 718 bytes in size.

FIELD OF THE INVENTION

The present invention relates to vaccination against animal pathogens using alphavirus-replicon RNA particles and oil adjuvants. To a vaccine, and a kit of parts comprising the replicon particles and the oil adjuvant. Also to methods and uses of making and using the vaccine and the components of the kit.

BACKGROUND

A number of vector based strategies have been employed through the years for vaccines in an effort to protect against animal pathogens. One such vector strategy includes the use of alphavirus-derived replicon RNA particles (RP) [Vander Veen, et al. Anim Health Res Rev. 13(1): 1-9 (2012) doi: 10.1017/S1466252312000011; Kamrud et al., J Gen Virol. 91(Pt 7): 1723-1727 (2010)] which have been developed from several different alphaviruses, including Venezuelan equine encephalitis virus (VEE) [Pushko et al., Virology 239: 389-401 (1997)], Sindbis virus [Bredenbeek et al., Journal of Virology 67: 6439-6446 (1993)], and Semliki Forest virus [Liljestrom and Garoff, Biotechnology (NY) 9: 1356-361 (1991)]. The encoded pathogenic antigens are expressed by the replicon particle, after its infection of a cell of a human or animal target. The result is the induction of protective antibodies against the expressed antigen. RPs have an attractive safety and efficacy profile when compared to some traditional vaccine formulations [Vander Veen, et al., Anim Health Res Rev. 13(1): 1-9 (2012)]. The RP platform is the basis for several USDA-licensed vaccines, which include: Porcine Epidemic Diarrhea Vaccine, RNA Particle (Product Code 19U5.P1), Porcine Influenza Vaccine, RNA (Product Code 19A5.D0), Avian Influenza Vaccine, RNA (Product Code 1905.D0), and Prescription Product, RNA Particle (Product Code 9PP0.00).

Alphavirus-derived replicon RNA particles lack the alphavirus structural protein genes, but maintain the replication elements necessary for cytoplasmic RNA self-amplification, and the expression of inserted heterologous nucleic acids, driven by the highly active 26S alphavirus subgenomic promoter. Accordingly, RPs are single-cycle infectious particles, that are replication-defective due to the absence of structural protein genes. [Lundstrom, *Vaccines* 6: 2392-2415 (2014)]. The structural proteins necessary for packaging and production of replicon particles therefore must be provided in trans in suitable host cells, to produce the RPs [see, Vajdy et al., *Immunol. and Cell Biol.* 82: 617-627 (2004)]. The structural proteins are generally provided for by the transient cotransfection of the replicon RNA and one or more 'helper' RNA's encoding the structural proteins. Alternatively RP can be produced from packaging cell lines that express the viral structural proteins, constitutively or transiently, from one or more DNA expression cassettes. In this way, the production of the replicon particles preserves the replication-defective nature of the vectors, as the structural proteins are not included within the resulting RP genome [Polo et al. *Dev. Biol.,* 104: 181-185 (2000)]. These replication-defective alphavirus RNA replicon particles when used for the immunization of a target human or animal, induce protective immune responses in vivo. VEE-based alphavirus vectors for example, elicit strong mucosal and systemic immune responses following systemic immunization of mice and larger animals [Davis et al., *IUBMB Life* 53: 209-211 (2002)].

Adjuvants are known compounds that are capable of providing an nonspecific stimulation to the immune system of a target human or animal. The standard use of adjuvants is in vaccines based on inactivated- or subunit antigens. A wide variety of adjuvant types and compositions exist, for example: aluminium salts such as Aluminium-hydroxide, or Aluminium-phosphate, liposomes, glucans, alginate, bacterial components such as cell-wall components, mineral- or non-mineral oils, synthetic adjuvants such as: non-ionic block polymers, polyamines such as dextran sulphate, Carbopol™, pyran, and Saponins, such as: Quil A™, or Q-vac™. Saponin and vaccine components may be combined in an ISCOM™.

Furthermore, peptides such as muramyldipeptides, dimethylglycine, tuftsin, are often used as adjuvant. Similarly, combination products such as the ISA™ compositions (Seppic, France).

A handbook on adjuvants and their uses and effects is: "Vaccine adjuvants" (Methods in molecular medicine, vol. 42, D. O'Hagan ed., 2000, Humana press, NJ, ISBN: 0896037355).

The citation of any reference herein should not be construed as an admission that such reference is available as "prior art" to the instant application.

SUMMARY OF THE INVENTION

The present invention provides a vaccine comprising an alphavirus RNA replicon particle encoding an antigen originating from an animal pathogen, wherein the vaccine also comprises an oil adjuvant.

In an embodiment of the vaccine of the invention, the oil adjuvant comprises at least one oil selected from a mineral oil and a non-mineral oil.

In an embodiment of the vaccine of the invention, the oil adjuvant comprises a mineral oil; preferably the mineral oil is a liquid paraffin oil.

In an embodiment of the vaccine of the invention, the oil adjuvant comprises a non-mineral oil; preferably the non-mineral oil is selected from a synthetic oil, a semi-synthetic oil, an animal oil, and a vegetable oil. More preferably the non-mineral oil is selected from a squalane, a squalene, a tocopherol and a vegetable oil. In an embodiment the tocopherol is an alpha-tocopherol; more preferably, the alpha-tocopherol is selected from Vitamin E and Vitamin E-acetate. In an embodiment the vegetable oil is an oleate, more preferably ethyl-oleate.

More preferably the non-mineral oil is squalane.

In a preferred embodiment of the vaccine of the invention, the oil adjuvant comprises more than one oil.

In an embodiment of the oil adjuvant comprising more than one oil, the adjuvant comprises a mineral oil and one or more non-mineral oils. More preferably the oil adjuvant comprises a liquid paraffin oil as the mineral oil, and one or more non-mineral oils selected from squalane, squalene, vitamin E, vitamin E-acetate, oleate, and ethyl-oleate. Still more preferably, the oil adjuvant comprises a liquid paraffin oil and vitamin E-acetate. Most preferably the oil adjuvant is XSolve™.

In an alternate embodiment of the oil adjuvant comprising more than one oil, the adjuvant comprises more than one non-mineral oil. Preferably the oil adjuvant comprises more than one non-mineral oil selected from squalane, squalene, vitamin E, vitamin E-acetate, oleate, and ethyl-oleate. Still more preferably, the oil adjuvant comprises squalane and vitamin E-acetate. Most preferably the oil adjuvant is SVEA™.

In an embodiment of the vaccine of the invention, the amount of the mineral oil in the oil adjuvant is 1-70% v/v of the oil adjuvant. Preferably the oil adjuvant comprises an amount of mineral oil of 5-60% v/v of the oil adjuvant.

In an embodiment of the vaccine of the invention, the total amount of the non-mineral oil is 0.1-30% w/v of the oil adjuvant. Preferably the oil adjuvant comprises a total amount of non-mineral oil of 0.5-25% v/v of the oil adjuvant.

In an embodiment, when the non-mineral oil comprises squalane, the oil adjuvant comprises squalane at 0.5-30% w/v of the oil adjuvant; more preferably the oil adjuvant comprises squalane at 1-25% w/v, at 2-15% w/v, or even comprises squalane at 3-10% w/v of the oil adjuvant.

Alternatively or additionally, in an embodiment when the non-mineral oil comprises vitamin E acetate, the oil adjuvant comprises vitamin E-acetate at 0.1-30% w/v of the oil adjuvant; more preferably the oil adjuvant comprises vitamin E-acetate at 0.5-20% w/v, at 1-16% w/v, or even comprises vitamin E-acetate at 2-10% w/v of the oil adjuvant.

In an embodiment of the vaccine of the invention, the oil adjuvant is formulated as an emulsion of an oil and an aqueous phase. Preferably the oil adjuvant is formulated as an oil-in-water (O/W) emulsion.

In an embodiment the aqueous phase comprises water of pharmaceutically acceptable quality.

In an embodiment the emulsion of the oil adjuvant is formulated as a micro-emulsion, wherein the droplets of the internal phase are smaller than 1 micrometer. Preferably the micro-emulsion is an O/W emulsion, more preferably the O/W micro emulsion is prepared using high energy homogenization, even more preferably prepared by a method of microfluidisation.

In an embodiment of the vaccine of the invention, the emulsion of the oil adjuvant comprises an emulsifier, preferably the emulsifier comprises a Polysorbate, more preferably the emulsifier comprises a Polysorbate 80.

In an embodiment the vaccine of the invention comprises an emulsion of the oil adjuvant, preferably the vaccine comprises the oil adjuvant formulated as an O/W emulsion.

In an embodiment of the vaccine of the invention, the vaccine is formulated as an oil-in-water (O/W) emulsion.

In an embodiment of the vaccine of the invention, the alphavirus RNA replicon particle is a Venezuelan Equine Encephalitis (VEE) alphavirus RNA replicon particle. In a more specific embodiment the VEE alphavirus RNA replicon particle is a TC-83 VEE alphavirus RNA replicon particle. In other embodiments, the alphavirus RNA replicon particle is a Sindbis alphavirus RNA replicon particle. In still other embodiments, the alphavirus RNA replicon particle is a Semliki Forest Virus alphavirus RNA replicon particle.

In an embodiment of the vaccine of the invention, for the encoded antigen originating from an animal pathogen, the animal pathogen is selected from a virus, a bacterium, a parasite, a protozoan, a fungus, a *rickettsia*, and a prion. More preferably the encoded antigen originating from an animal pathogen is an antigen originating from a virus or a bacterium. Most preferably the antigen is from a virus.

In an embodiment of the vaccine of the invention, the RP encodes an antigen originating from an animal pathogen, whereby the animal is an animal of relevance to veterinary science. Preferably the animal is selected from a fish, an avian, and a mammal. More preferably the animal is a wild-, a livestock-, or a companion animal. A livestock animal is a fish, avian, porcine, or ruminant; preferably the porcine is a pig; preferably the avian is a chicken, turkey, duck, geese, quail, or ostrich; preferably the ruminant is a cow, sheep, goat, buffalo, camel or deer; preferably the fish is a bony fin fish, more preferably a salmonid- or a cichlid fish (i.e. a member of the Cichlidae family). The salmonid fish is preferably selected from Atlantic-, steelhead-, chinook-, coho-, pink-, chum-, and sockeye salmon, rainbow-, brook-, lake-, and brown trout, and char. The cichlid fish is preferably a Tilapia. The companion animal is preferably selected from a cat, dog and equine. More preferably the animal is a Tilapia, a chicken, or a pig.

In an embodiment of the vaccine of the invention, the nucleotide sequence of the gene encoding the antigen originating from an animal pathogen of the invention is optimized for expression in the cells of the target animal species for the vaccine. In an embodiment the nucleotide sequence optimization is a codon-optimization. In an embodiment the nucleotide sequence optimization is an optimization of the secondary structure of the RNA transcript.

In a preferred embodiment, the nucleotide sequence optimization of the gene encoding the antigen originating from an animal pathogen of the invention regards both the codon usage and the secondary structure of the RNA transcript. Preferably the nucleotide sequence optimization is done according to the procedures described in one or more of U.S. Pat. Nos. 7,561,972, 7,561,973, 7,805,252, and 8,126,653.

In a particularly preferred embodiment of the vaccine of the invention, the oil adjuvant comprises a mineral oil and a non-mineral oil, the vaccine is formulated as an O/W emulsion, the alphavirus RNA replicon particle is a VEE alphavirus RNA replicon particle, the antigen of an animal pathogen is an antigen of a virus, and the virus is a pathogen of a porcine.

In a preferred embodiment of the vaccine of the invention, the encoded antigen originating from an animal pathogen is a hemagglutinin (HA)- or a neuraminidase (NA) protein of an influenza virus, or an antigenic fragment of such HA or NA protein. The HA and/or the NA protein preferably originate from an Influenza virus type A, more preferably originate from a porcine influenza A virus or from PEDV.

The present invention further provides multivalent vaccines comprising the alphavirus RNA replicon particles of the present invention, wherein the vaccine comprises more than one RP encoding an antigen, or the vaccine comprises one or more RPs each encoding one or more than one antigen for the invention.

The vaccine of the invention comprises an immunologically effective amount of the alphavirus RNA replicon particles for the invention. In an embodiment the vaccine comprises from about 1×10^9 to about 1×10^11 RPs. In more particular embodiments, the vaccine comprises from about 1×10^4 to about 1×10^10 RPs. In even more particular embodiments, the vaccine comprises from about 1×10^5 to about 1×10^9 RPs.

The vaccine of the invention comprises an immunologically effective amount of the oil adjuvant for the invention. In an embodiment the vaccine comprises the oil adjuvant in an amount of between about 10%-90% v/v of the vaccine. More preferably the vaccine comprises the oil adjuvant in an amount of between about 20%-80% v/v, 30-70% v/v, or even 40-60% v/v of the vaccine. Most preferred, the vaccine comprises the oil adjuvant in an amount of about 50% v/v of the vaccine.

In particular embodiments the vaccine of the present invention is administered in a volume per animal dose of 0.05 mL to 5 mL. In more particular embodiments, the dose administered per animal is 0.1 mL to 2 mL. In still more particular embodiments, the dose administered is 0.2 mL to 1.5 mL. In even more particular embodiments, the dose administered is 0.3 to 1.0 mL. In still more particular embodiments, the dose administered per animal is 0.4 mL to 0.8 mL.

In an embodiment of the vaccine of the invention, the vaccine comprises a further adjuvant. Preferably the further adjuvant is selected from the group of: a bacterial cell-wall component, a cytokine, and an immunostimulatory nucleic acid comprising an unmethylated CpG. In an embodiment the immunostimulatory nucleic acid is one or more selected from WO 2012/089.800 (X4 family), WO 2012/160.183 (X43 family), and WO 2012/160.184 (X23 family).

In an embodiment of the vaccine of the invention, the vaccine comprises a further antigen of an animal pathogen. In a preferred embodiment the further antigen is selected from the group of: a live attenuated micro-organism, an inactivated micro-organism, and a subunit of a micro-organism.

In a further aspect the invention provides for a kit of parts, the kit comprising at least two containers, whereby at least one container is comprising the alphavirus RNA replicon particle encoding an antigen originating from an animal pathogen, and at least one container is comprising the oil adjuvant. The at least two containers each comprise the alphavirus RNA replicon particle, or the oil adjuvant, in immunologically effective amounts.

In preferred embodiments of the kit of parts of the present invention, one or more or all of: the alphavirus RNA replicon particle, the encoded antigen, the animal pathogen, and the oil adjuvant, are as defined in any one or more of the embodiments as described herein.

In preferred embodiments the at least one container comprising the RP is comprising the RP as a lyophilisate.

In an alternate embodiment the at least one container comprising the RP is comprising the RP in an aqueous solution; the aqueous solution preferably comprising a buffer; the aqueous solution is preferably kept cooled or frozen. In an embodiment the aqueous solution is a reconstituted RP solution, generated from the admixing of the RP lyophilisate and a suitable aqueous diluent.

In the embodiment wherein the at least one container comprises the RP as a lyophilisate, the kit of parts for the invention can comprise a further container containing a suitable diluent for reconstituting the lyophilized RP. In a preferred embodiment the diluent is an aqueous solution, preferably comprising a buffer and/or a stabilizer and water of pharmaceutically acceptable quality.

In a preferred embodiment, the container comprising the oil adjuvant is comprising the oil adjuvant formulated as an emulsion of an oil and an aqueous phase; preferably the emulsion is an oil-in-water emulsion.

In an embodiment of the kit of parts, the kit comprises instructions for use of the kit and/or of its component parts. In preferred embodiments the instructions for use are provided on or with one or more of the component parts of the kit; or are provided by way of a reference to instructions in electronic form, such as information viewable on, or downloadable from an internet website from the manufacturer, or the distributor of the kit.

In an embodiment the kit of parts is a box comprising the at least two containers, and instructions for use displayed on an information carrier (e.g. a card, or a leaflet) comprised with or within the box.

In an embodiment of the kit of parts, the kit may also be an offer of the component parts (relating to commercial sale), for example on an internet website, for use in a method of immunizing of the invention.

In an embodiment of the kit of parts, one or more of the containers may comprise a further adjuvant as described herein; also or alternatively, one or more of the containers may comprise a further antigen of an animal pathogen as described herein.

The alphavirus RNA replicon encoding an antigen originating from an animal pathogen, and the oil adjuvant, both as defined herein, can be administered to a target animal. Such administration will induce an effective immune-protection in said animal against infection or disease caused by the animal pathogen. The administration can be performed for example along the guidelines of the EMA—CVMP for the associated use of immunological veterinary medicinal products.

Therefore, in a further aspect the invention provides for a method of immunizing an animal comprising administering to the animal immunologically effective amounts of an alphavirus RNA replicon particle encoding an antigen originating from an animal pathogen, and of an oil adjuvant.

In a preferred embodiment of the method of immunizing an animal of the present invention, the method comprises administering to the animal the vaccine of the invention.

In preferred embodiments of the method of immunizing an animal of the present invention, one or more or all of: the alphavirus RNA replicon particle, the encoded antigen, the animal pathogen, and the oil adjuvant, are as defined in any one or more of the embodiments as described herein.

In preferred embodiments of the method of immunizing an animal of the present invention, the encoded antigen originating from an animal pathogen is an antigen originating from a pathogen from a fish, a member of the Cichlidae family, a Tilapia, a mammal, an avian, and a chicken.

In an embodiment of the method of immunizing an animal of the invention, the alphavirus RNA replicon particle and the oil adjuvant are administered in or on the target animal body in simultaneous use or in concurrent use.

In a preferred embodiment of the method of immunizing an animal of the invention, the alphavirus RNA replicon particle and the oil adjuvant are administered in or on the target animal body in simultaneous use, i.e. as a single composition.

In a preferred embodiment the single composition is the vaccine of the invention.

In a preferred embodiment the single composition is prepared shortly before the administration to the target animal by the admixing of a composition comprising the RP and a composition comprising the oil adjuvant, both as described for the invention; more preferably by the admixing of the contents of the containers of the kit of parts of the invention; even more preferably by admixing an aqueous solution comprising the RPs and a composition comprising an O/W emulsion of the oil adjuvant. In an alternate even more preferred embodiment, the single composition is prepared by reconstituting the RP lyophilisate with the O/W emulsion of the oil adjuvant, both as defined herein for the invention. Effectively, the preparation of the single composition generates the vaccine of the invention.

Preferably "shortly before the administration to the target animal" is within 24 hours before administration to the target animal, more preferably within 16 hours, within 12 hours, within 8 hours, within 4 hours, or even within 2 hours before administration to the target animal, in this order of preference.

In an alternate preferred embodiment of the method of immunizing an animal of the invention, the alphavirus RNA replicon particle and the oil adjuvant are administered in or on the target animal body in concurrent use, i.e. as comprised in separate compositions, which are administered separated in place and/or in time.

In a preferred embodiment the concurrent use comprises the administration in or on the target animal body, but separated in place and/or in time, of the alphavirus RNA replicon particle and of the oil adjuvant as comprised in the kit of parts of the invention.

In a preferred embodiment of the concurrent use of the invention, the separate compositions are administered to the separate sites in or on the target animal body, by the same or by different routes of administration, within a limited amount of time of each other; preferably the "limited amount of time" is within 2 weeks of each other, more preferably within 1 week of each other, even more preferably within 1 day, within 16 hours, within 12 hours, within 8 hours, within 4 hours, within 2 hours, within 1 hour, within 30 minutes, or even within 10 minutes of each other, in this order of preference. Most preferably the concurrent use administration is substantially simultaneous.

In a preferred embodiment of the concurrent use of the invention, the separate compositions are administered within the limited amount of time of each other, in or on the target animal body, by the same or by different routes of administration, at separate sites. For the invention, the separate sites of the administration are separated on or in the animal body by at least 1 cm between each other; preferably by at least 2 cm, by at least 5 cm, by at least 10 cm, or even by at least 25 cm between each other, in this order of preference.

In a preferred embodiment of the concurrent use of the invention, the separate compositions are administered within the limited amount of time of each other, in or on the target animal body, by the same or by different routes of administration, at substantially the same site in or on the target animal body but sufficiently separated from each other in time to prevent mixing of the compositions at the site of administration. For the invention, sufficient separation in time to prevent mixing is not within 2 hours of each other, preferably not within 6 hours, not within 12 hours, not within one day, not within 2 days, or even not within one week of each other, in this order of preference.

In an embodiment of the method of immunizing an animal of the invention, the administration in or on the target animal body, is performed by parenteral administration. In an alternative embodiment the administration is by a method of mucosal administration. In still an alternative embodiment the vaccine is administered by a method of topical administration.

Preferred method of administration is selected from intradermal, intramuscular, intraperitoneal, subcutaneous, immersion and spray. The intradermal method of administration is preferably by a needle-free way of administration, more preferably by using an IDAL® device (Intra-Dermal Application of Liquids).

In an embodiment of the administration of the vaccine of the invention, the vaccine is administered as a primer vaccine and/or as a booster vaccine. In specific embodiments, a vaccine of the present invention is administered as a one time (one shot) vaccination, without requiring subsequent booster administrations. In certain embodiments, in the case of the administration of both a primer vaccine and a booster vaccine, the primer vaccine and the booster vaccine are administered by the identical route. In alternative embodiments, in the case of the administration of both a primer vaccine and a booster vaccine, the administration of the primer vaccine is performed by one route and the booster vaccine by another route.

In certain embodiments of the administration of the vaccine of the invention, the vaccine is administered to porcine and the primer vaccine and the booster vaccine are both administered by intradermal injection. In an alternate embodiment, the primer vaccine is administered by intradermal injection and the booster vaccine is administered by another route.

In a further aspect, the invention provides for a method for the production of a vaccine of the present invention, the method comprising the step of admixing the alphavirus RNA replicon particle encoding an antigen originating from an animal pathogen, and the oil adjuvant. Both the alphavirus RNA replicon particle and the oil adjuvant are admixed at immunologically effective amounts.

In preferred embodiments of the method for the production of a vaccine of the present invention, one or more or all of: the vaccine, the alphavirus RNA replicon particle, the encoded antigen, the animal pathogen, and the oil adjuvant, are as defined in any one or more of the embodiments as described herein.

In an embodiment of a method for the production of a vaccine of the present invention the alphavirus RNA replicon particle is comprised in an aqueous solution.

In a preferred embodiment of a method for the production of a vaccine of the present invention the admixing is performed such that the alphavirus RNA replicon particle, respectively the aqueous solution comprising the alphavirus RNA replicon particle, and the oil adjuvant, are admixed in a volume ratio of between 1:10 to 10:1; more preferably in a volume ratio of between 1:5 to 5:1, between 1:4 to 4:1, between 1:3 to 3:1, or even between 1:2 to 2:1, in this order of preference. Most preferably the alphavirus RNA replicon particle, respectively the aqueous solution comprising the alphavirus RNA replicon particle, and the oil adjuvant are admixed in a volume ratio of about 1:1.

In an embodiment the method for the production of the vaccine of the present invention comprises the admixing of the contents of the containers of the kit of parts of the present invention.

In an embodiment of a method for the production of a vaccine of the present invention, the alphavirus RNA replicon particle, respectively an aqueous solution comprising the replicon particle, is admixed with an oil adjuvant as defined for the invention that is comprised in another O/W emulsion comprising an antigen of a pathogen. Preferably the other O/W emulsion is a vaccine comprising an inactivated viral- and/or bacterial pathogen. In a more preferred embodiment, an RP encoding an antigen from SIV or from PEDV is admixed with an O/W emulsion vaccine comprising porcine circovirus (PCV) and/or *Mycoplasma hyopneumoniae*, such as Circumvent® PCVM.

In a further aspect, the invention provides for an alphavirus RNA replicon particle encoding an antigen originating from an animal pathogen, for use in the protection of an animal against infection or disease caused by the animal pathogen, wherein the alphavirus RNA replicon particle is administered in or on the target animal body in simultaneous use or in concurrent use with an oil adjuvant. Both the alphavirus RNA replicon particle and the oil adjuvant are comprised in the use in the protection of an animal, at immunologically effective amounts.

In preferred embodiments of the alphavirus RNA replicon for use in the protection of the present invention, one or more or all of: the alphavirus RNA replicon particle, the encoded antigen, the animal pathogen, and the oil adjuvant, are as defined in any one or more of the embodiments as described herein.

In a preferred embodiment of the alphavirus RNA replicon for use in the protection of the present invention, the use comprises the use of the vaccine of the invention.

In an embodiment of the alphavirus RNA replicon for use in the protection of the present invention, the protection is effective in target animals of different ages and types.

In an embodiment the use is for the protection of young animals. Preferably young animals are porcines up to 3 weeks of age, or chickens up to 1 week of age, or salmonid fish up to 14 months of age.

In a further embodiment the use is for the protection of adolescent animals. Preferably adolescent animals are porcines of between 3 weeks and 8 months of age, or chickens of between 1 and 22 weeks of age, or are salmonid fish between 14 and 24 months of age.

In a further embodiment, the use is for the protection of adult animals. Preferably adult animals are porcines of over 8 months of age, or chickens of over 22 weeks of age, or are salmonid fish of over 24 months of age.

For Tilapia the preferred periods for use for the protection of the invention are commonly expressed not by age, but by indication of a range of whole bodyweight: vaccination by immersion bath treatment is preferably done when the Tilapia weigh between 0.5 g and 5 g. Vaccination by parenteral injection is preferably done when the Tilapia weigh between 10 g and 100 g; more preferably when the Tilapia weigh between 20 g and 25 g.

In an embodiment of the alphavirus RNA replicon for use in the protection of the present invention, the target animal can be seropositive or seronegative, either for antibodies to the animal pathogen, or for the animal pathogen, respectively for an antigen from the animal pathogen.

In an embodiment of the alphavirus RNA replicon for use in the protection of the present invention, the target animal is an animal positive for MDA (maternally derived antibodies), whereby the MDA are reactive with the animal pathogen against which the protection is intended. More preferably the animal positive for MDA is an avian, a ruminant or a pig. Still more preferably the animal positive for MDA is a pig.

In an embodiment of the alphavirus RNA replicon for use in the protection of the present invention, the target animal is a pregnant animal. More preferably the pregnant animal is a ruminant or a pig. Still more preferably the pregnant animal is a pig.

In an embodiment of the alphavirus RNA replicon for use in the protection of the present invention, the protection is of production animals. Preferably production animals are porcines kept for fattening, or are broiler- or layer chickens, or are ruminants kept for producing milk or meat, or are salmon, or are Tilapia.

In a further embodiment the protection is of animals for restocking populations. Preferably animals for restocking populations are parental- or grand-parental lines of production animals.

In a further aspect, the invention provides for the use of an alphavirus RNA replicon particle encoding an antigen originating from an animal pathogen, for the manufacture of a vaccine for the protection of an animal against infection or disease caused by the animal pathogen, comprising the simultaneous use or the concurrent use of said alphavirus RNA replicon particle with an oil adjuvant. Both the alphavirus RNA replicon particle and the oil adjuvant are used at immunologically effective amounts.

In preferred embodiments of the use for the manufacture of a vaccine of the present invention, one or more or all of: the alphavirus RNA replicon particle, the encoded antigen, the animal pathogen, and the oil adjuvant, are as defined in any one or more of the embodiments as described herein.

In a further aspect, the invention provides for the use of an alphavirus RNA replicon particle encoding an antigen originating from an animal pathogen, for the manufacture of a component of a kit of parts as defined herein for the invention, whereby the kit is for the protection of an animal against infection or disease caused by the animal pathogen, by the simultaneous use or the concurrent use of the components of said kit. Both the alphavirus RNA replicon particle and the oil adjuvant are used at immunologically effective amounts.

In preferred embodiments of the use for the manufacture of a component of a kit of parts of the present invention, one or more or all of: the alphavirus RNA replicon particle, the encoded antigen, the animal pathogen, the oil adjuvant, and the kit of parts, are as defined in any one or more of the embodiments as described herein.

In a further aspect, the invention provides for the use of an alphavirus RNA replicon particle encoding an antigen originating from an animal pathogen, for the protection of an animal against infection or disease caused by the animal pathogen, wherein the use comprises the simultaneous use or the concurrent use of said alphavirus RNA replicon particle with an oil adjuvant. Both the alphavirus RNA replicon particle and the oil adjuvant are used at immunologically effective amounts.

In preferred embodiments of the use for the protection of an animal of the present invention, one or more or all of: the alphavirus RNA replicon particle, the encoded antigen, the animal pathogen, and the oil adjuvant, are as defined in any one or more of the embodiments as described herein.

These and other aspects of the present invention will be better appreciated by reference to the following Figures and the Detailed Description.

BRIEF DESCRIPTION OF THE FIGURES

FIGS. 1A-1B: Lung Lesions

FIGS. 1C-1D: Nasal shedding

FIGS. 1E-1F: NI titers

FIG. 2A-2F: HI titer results (figures numbered left to right, top row then bottom row)

Represented are the serum neuraminidase inhibition (NI) antibody responses specific to N1-classic strain of the vaccine compositions as described in Example 3. The serum samples were collected prior to first vaccination (3 weeks of age), prior to second vaccination (7 weeks of age), and prior to challenge (10 weeks of age).

Figure 4:
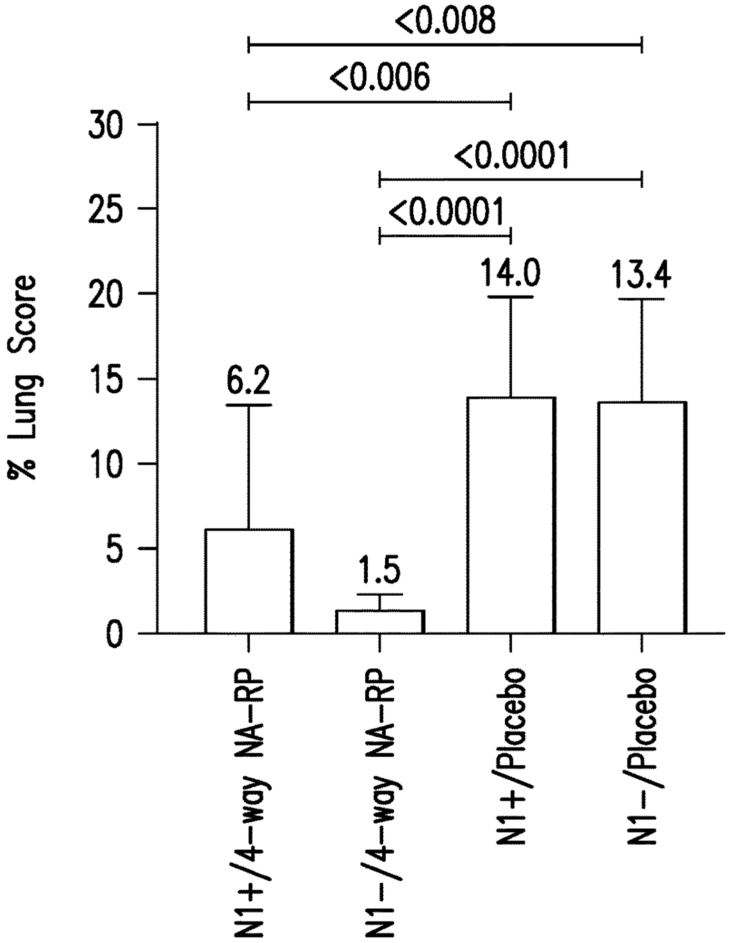

FIG. 4: Efficacy of 4-way NA-RP vaccine against challenge infections, as tested in Example 3, regarding to macroscopic lung lesions scores at 5 days post infection with H1N1 virus:

This shows the lung lesion scores of pigs following administration of the vaccination compositions described in Example 3 and the challenge infection with H1-gamma-N1-classic virus.

Figure 5:
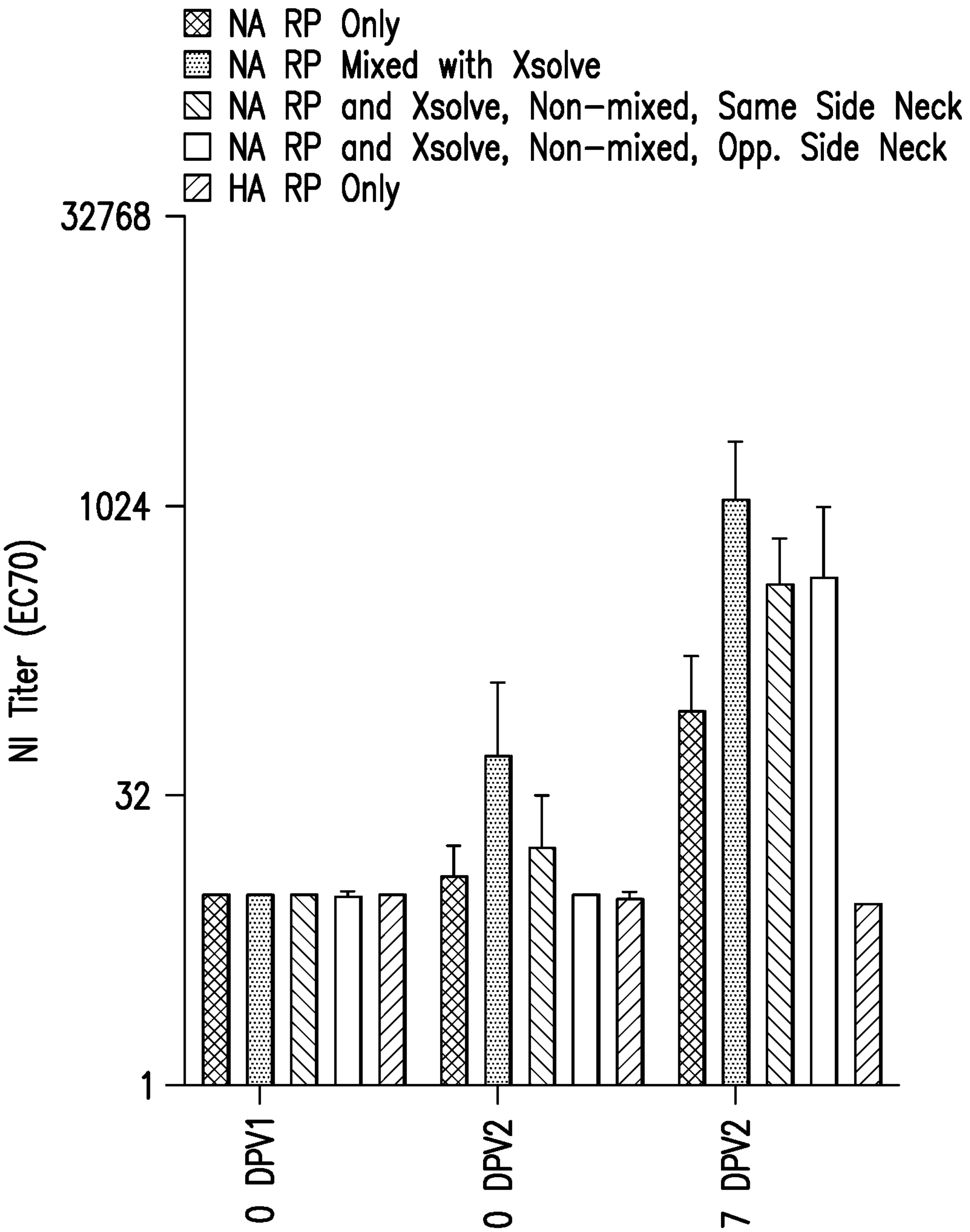
Figure 6:
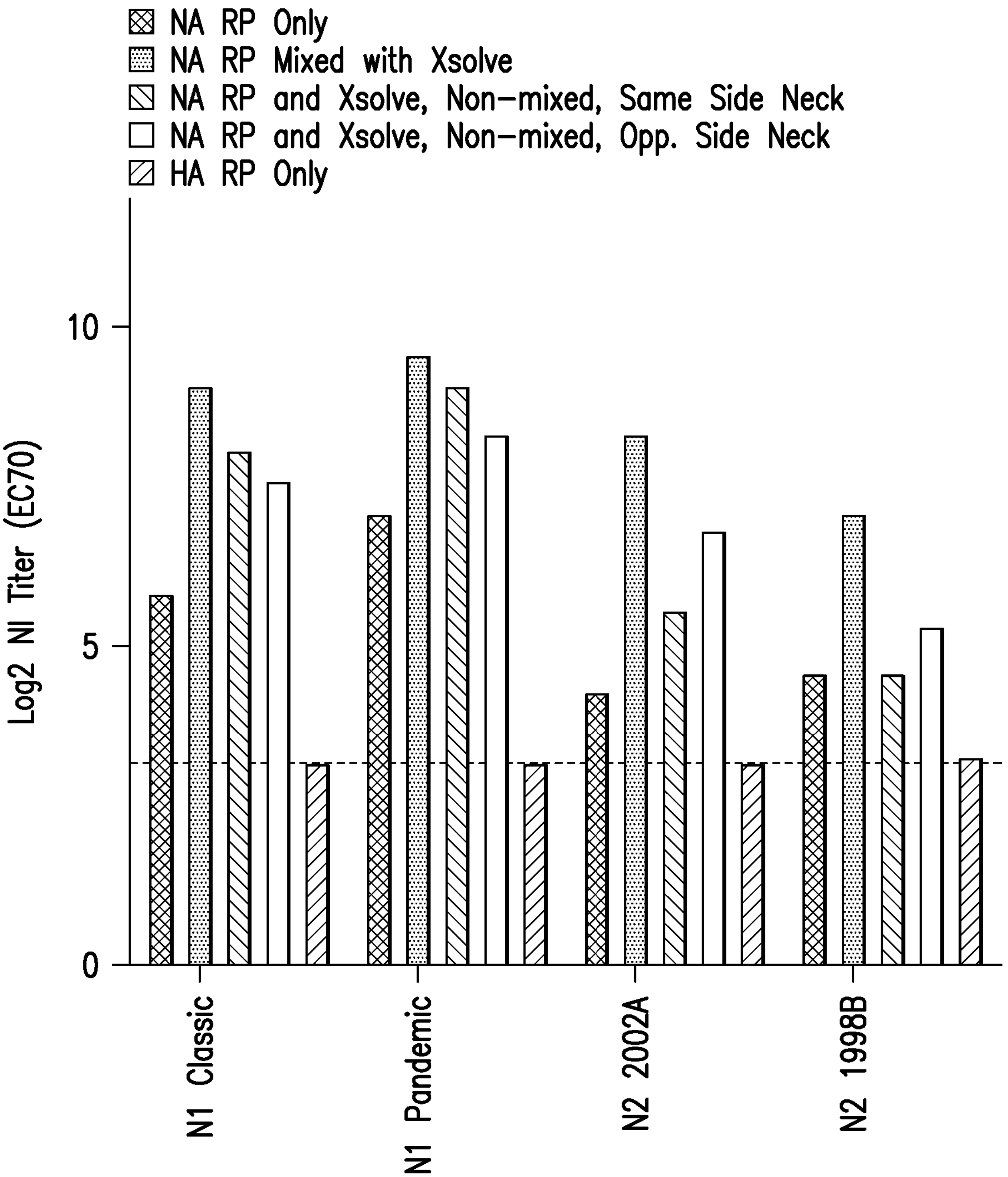

FIGS. 5 and 6: Results of NI titers from Example 8:

FIG. 5 presents the NI titers against the N1 classic NA antigen at the three time points measured over time, including the standard deviations. This is representative of the NI titer profile measured for the other three NA types.

FIG. 6 presents the group mean NI titers of the combined 4 NA types, at 7 days post second vaccination.

DETAILED DESCRIPTION OF THE INVENTION

The present invention provides vaccines that include an immunologically effective amount of one or more alphavirus RNA replicon particles that encode one or more antigen of an animal pathogen, and an oil adjuvant. Alphavirus RNA replicon particles are effectively similar to a live virus in that they can infect host cells of a target human or animal and express the genes they comprise. This is also demonstrated by the fact that RPs are commonly quantified by infectivity-titration on cells. Therefore such RPs, in a pharmaceutically acceptable carrier, are commonly the sole component of an effective vaccine, similar to a live (attenuated) viral vaccine. Several vaccines based on unadjuvanted RPs have been developed and commercialized.

Adjuvants are mainly used only in combination with killed- or subunit vaccine antigens. Also, oil adjuvants can be quite aggressive for other vaccine constituents, therefore oil adjuvants are not commonly combined with live vaccines. Further, vaccines of alphavirus RNA RPs, especially those based on VEE alphavirus, are known to induce-next to an acquired immune response-already by themselves a strong antiviral response from the target's innate immune system. Thereby effectively preventing any need for additional immunostimulation.

Nevertheless, it was surprisingly found that an oil adjuvant could significantly enhance the immunogenic efficacy of alphavirus RNA replicon particles encoding an antigen originating from an animal pathogen. This in contrast to an adjuvant based on Aluminium, such as aluminium-hydroxide. The enhanced efficacy could be obtained both when the RPs and oil adjuvant were applied when combined into a single composition (i.e. simultaneous use), or when they were administered as separate compositions (i.e. concurrent use). The extent of the efficacy enhancement by an oil adjuvant was also unexpected, as the minimal effective dose of RPs could be reduced by several orders of magnitude, for a vaccination with RP and oil adjuvant, as compared to one without (oil) adjuvant. Further the use of oil adjuvant was able to increase the duration of the immune response from an RP vaccination. Also, the combination of oil adjuvant and RP was capable of providing an excellent immune response when the RP component alone induced no immunization at all.

In order to more fully appreciate the invention, the following definitions are provided.

A "vaccine" is a well-known composition with a medical effect, that comprises an immunologically active component, and a pharmaceutically acceptable carrier. The aqueous solution and/or the oil adjuvant can function as a 'carrier' for the vaccine. The 'immunologically active component' for the vaccine of the invention is the encoded antigen originating from an animal pathogen, which is delivered and expressed by way of the RP. The vaccine stimulates the immune system of a vaccinated target animal, which induces a protective immunological response. The response may originate from the animal's innate- and/or from the acquired immune system, and may be of the cellular- and/or of the humoral type.

A vaccine provides "protection" "against infection or disease" by reducing in a vaccinated animal the severity of a subsequent infection or infestation, for example by reducing the number of pathogens, or shortening the duration of the pathogen's replication in or on the animal, and reducing the number, the intensity, or the severity of lesions caused by an infection or infestation. Also, or consequentially, a vaccine is effective in reducing or ameliorating the (clinical) symptoms of disease that may be caused by such infection, infestation or replication, or by the target's response to that infection, infestation or replication. A reference for such diseases and clinical signs is: "The Merck veterinary manual" (10th ed., 2010, C. M. Kahn edt., ISBN: 091191093X). Such a vaccine is colloquially referred to as a: vaccine 'against' the particular pathogen.

The term "comprising" (as well as variations such as "comprise", "comprises", and "comprised") as used herein, refer(s) to all elements, and in any possible combination conceivable for the invention, that are covered by or included in the text section, paragraph, claim, etc., in which this term is used, even if such elements or combinations are not explicitly recited; and does not refer to the exclusion of any of such element(s) or combinations. Consequently, any such text section, paragraph, claim, etc., can also relate to one or more embodiment(s) wherein the term "comprises" (or its variations) is replaced by terms such as "consist of", "consisting of", or "consist essentially of".

As used herein, the term "replicon" refers to a modified RNA viral genome that lacks one or more elements (e.g., coding sequences for structural proteins) that if they were present, would enable the successful propagation of the parental virus in cell cultures or animal hosts. In suitable cellular contexts, the replicon will amplify itself and may produce one or more sub-genomic RNA species.

As used herein, the term "alphavirus RNA replicon particle", abbreviated "RP", is an alphavirus-derived RNA replicon packaged in viral structural proteins, e.g., the capsid and glycoproteins, which also are derived from an alphavirus, e.g., as described by Pushko et al., [*Virology* 239(2): 389-401(1997)]. An RP infects a suitable target cell, and then expresses the inserted heterologous gene(s), but cannot propagate in cell cultures or animal hosts (without a helper plasmid or analogous component), because the replicon does not encode the alphavirus structural components (e.g., capsid and viral glycoproteins).

The use of singular terms for convenience in description is in no way intended to be so limiting. Thus, for example, reference to an "alphavirus RNA replicon particle" includes reference to a plurality of such alphavirus RNA replicon particles, unless otherwise indicated.

The RP "encoding" an antigen refers to the transcription and/or translation of the nucleic acid for that protein antigen that is comprised in the RP, resulting in the protein antigen being expressed. Typically such a nucleic acid encoding a protein is an open reading frame (ORF), indicating that no undesired stop codons are present that would prematurely terminate the translation of the protein. The nucleic acid may be a full gene encoding a complete protein, or may be a gene-fragment, encoding a section of a protein, for example encoding only the mature- or the secreted form of a protein, i.e. without a 'leader', 'anchor', or 'signal sequence'. The nucleotide sequence may be of natural- or of synthetic source.

The construction and manipulation of the heterologous nucleic acid sequence expressing the antigen for the invention can be done by well-known molecular biological techniques, involving cloning, transfection, recombination, selection, and amplification. These, and other techniques are explained in great detail in standard text-books like Sambrook & Russell: "Molecular cloning: a laboratory manual" (2001, Cold Spring Harbour Laboratory Press; ISBN: 0879695773); Ausubel et al., in: Current Protocols in Molecular Biology (J. Wiley and Sons Inc., NY, 2003, ISBN: 047150338X); C. Dieffenbach & G. Dveksler: "PCR primers: a laboratory manual" (CSHL Press, ISBN 0879696540); and "PCR protocols", by: J. Bartlett and D. Stirling (Humana press, ISBN: 0896036421).

For the invention, a "protein" is a molecular chain of amino acids. A protein can be a native or a mature protein, a pre- or pro-protein, or a part of a protein. Inter alia: peptides, oligopeptides and polypeptides are included within the definition of protein.

An "antigen" for the invention refers to a protein that can-in the right circumstances-induce a protective immunological response in a target animal.

The terms "originate from", "originates from" and "originating from" are used interchangeably with respect to a given protein antigen and the pathogen or strain of that pathogen that naturally encodes it. As used herein these terms signify that the unmodified and/or modified amino acid sequence of that given protein antigen is encoded by that pathogen or strain of that pathogen. The coding sequence within a nucleic acid construct of the present invention for a protein antigen originating from a pathogen, may have been genetically manipulated so as to result in a modification, truncation, and/or extension of the amino acid sequence of the expressed protein antigen relative to the corresponding encoding sequence of that protein antigen in the pathogen or strain of pathogen (including naturally attenuated strains) it originates from.

The "animal pathogen" refers to any biological entity capable of causing infection and/or disease in an animal of veterinary relevance, such as in wild-, livestock-, or companion animals.

For the invention, the animal pathogen may or may not be a natural pathogen of the target animal that is receiving the vaccine of the invention.

An "oil" is used here in its common meaning and refers to a nonpolar chemical substance with a relatively high hydro-carbon content that is typically a relatively viscous liquid, has a density lighter than water, and is hydrophobic and lipophilic. An oil can be of mineral origin, or of "non-mineral" origin such as of synthetic-, semi-synthetic-, animal- or vegetable origin. Some oils are metabolisable.

The term "mineral" indicates that the respective oil originates from a mineral source, typically from petroleum.

A "semi-synthetic oil" is an oil that is non-mineral in origin such as an animal or vegetable oil, but which was modified in structure and/or composition by a chemical or physical process.

The term "adjuvant" is used here in its common meaning of a composition capable of stimulating an immune response in a target animal in an nonspecific manner.

A "liquid paraffin oil", is a type of mineral oil, also named a white (mineral) oil, or light liquid paraffin oil, and has CAS number: 8042-47-5. It is generally available, also in pharmaceutical grade quality. Examples are: Drakeol® 6VR (Penreco), Marcol® 52 (Exxon Mobile), and Klearol® (Sonneborn).

A "vitamin E-acetate" refers to the chemical compound with CAS number: 58-95-7. Some alternate names are: tocopheryl acetate, or alpha-tocopherol-acetate. Vitamin E-acetate is an acetate-ester of vitamin E (tocopherol), and can be derived from vegetable materials such as seeds, nuts, fruits or leaves, or from fatty meats, but may also be produced synthetically. Thus, included in the definition of vitamin E-acetate are natural, synthetic or semi-synthetic forms, or mixtures thereof. Vitamin E-acetate is commercially available, in different degrees of purity.

A "squalane" refers to the chemical compound with CAS number 111-01-3. Some alternate names are: hydrogenated shark liver oil, hexamethyltetracosane, or perhydrosqualene. This is not to be confused with squalene (CAS nr. 111-02-4) which is a poly-unsaturated C30 oil and is metabolisable as a compound of the cholesterol pathway.

Originally the precursor to squalane was obtained from shark livers, but over environmental concerns this has shifted to other natural sources, such as olive oil, or to chemical synthesis. Therefore included in the definition of squalane are natural, synthetic or semi-synthetic forms, or mixtures thereof. Squalane is commercially available in a variety of purities, for example: from vegetable source, from Worlee (Squalane, vegetable), or Croda (Pripure™ Squalane); or synthetic, e.g. from Kuraray (Squalane-PE). For the invention, a high purity of the squalane is preferred: preferably over 75% purity, more preferably over 80, 90, or even over 95% purity, in that order of preference.

An "emulsion" is a mixture of at least two immiscible liquids, whereby one is dispersed in another. Typically the droplets of the dispersed phase are very small, in the range of micrometers or less. For the invention the emulsion comprises an oil and an aqueous phase.

Procedures and equipment for the preparation of an emulsion at any scale are well-known in the art, and are for instance described in handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

When the oil adjuvant for the invention is an emulsion, the emulsion can be a water-in-oil (W/O) emulsion, where the oil is the continuous outer phase. Alternatively, the emulsion can be an "oil-in-water" (O/W) emulsion, where the oil is the dispersed internal phase.

By the selection of the appropriate kind and concentration of emulsifier(s), such emulsions can be formed and stably maintained.

The emulsifier takes position at the interphase between water and oil and stabilizes the droplets of the internal, dispersed phase. Many different emulsifiers are known and are suitable for pharmaceutical use, such as in vaccines. Preferred emulsifier for the oil adjuvant of the invention is Polysorbate 80, also known as polyoxyethylene sorbitan mono-oleate, and commercially available as TWEEN®80. TWEEN®80 is used in the oil adjuvant for the invention in an amount of 0.1-10% w/v of the oil adjuvant.

For the present invention the oil adjuvant, when in the form of an O/W emulsion thus consists of an outer aqueous phase and a dispersed internal oil phase. This facilitates the admixing of the oil adjuvant as O/W emulsion with the RP encoding an antigen originating from an animal pathogen for the invention. For example by the admixing of an aqueous composition comprising the RP, with the oil adjuvant O/W emulsion. Simple handshaking for about 1 minute then suffices to properly mix the two aqueous compositions.

Alternatively, and highly advantageously, the oil adjuvant as an O/W emulsion can be used directly to reconstitute the RP from a lyophilized form. This means that the RP can be provided in a highly stabilized form as a lyophilisate, and the vaccine of the invention can be prepared by field-side mixing at a convenient time, before administration to a target animal.

As used herein the term "about" is used interchangeably with the term "approximately" and signifies that a value is within fifty percent of the indicated value i.e., a composition containing "approximately" 1×10^8 alphavirus RNA replicon particles per milliliter contains from 5×10^7 to 1.5×10^8 alphavirus RNA replicon particles per milliliter.

An example of an O/W emulsion oil adjuvant for the vaccine of the invention is: XSolve™ . XSolve™ is a combination of two O/W emulsion adjuvant components: Diluvac Forte™ which is based on vitamin E acetate (see EP 382.271), and Microsol™ which is based on liquid paraffin oil (see WO 2009/144.088).

In these emulsions, the volume average size of the oil droplets of the mineral- and of the non-mineral oil may be different. Preferably the droplets of the mineral oil are of submicron size.

Conveniently, the oil adjuvant emulsion is prepared separately from the RPs of the invention. Consequently methods and equipment for the emulsification of the oil adjuvant can be used which would not be compatible with maintaining the quality of the RPs, had these been present in the oil adjuvant. One example is a high shear emulsification method used to obtain a submicron emulsion by high pressure homogenization, such as with a Microfluidizer® processor (Microfluidics, MA, USA).

A further example of an O/W emulsion oil adjuvant for the vaccine of the invention is: SVEA™, which comprises squalane and Vitamin E-acetate, and is described in: WO 2018/115.435.

For the invention, the names of micro-organisms or pathogens, such as e.g. Venezuelan equine encephalitis virus (VEE) and Avian influenza virus, etcetera, refer to the respective taxonomic classifications of those micro-organisms as currently applicable. However those names could change in time as new insights can lead to reclassification into a new or different taxonomic group. However, as this does not change the micro-organisms itself, nor its antigenic repertoire, but only its scientific name or classification, such re-classified micro-organisms remain within the scope of the invention.

The reference to a taxonomic family includes any micro-organism that is a species, subtype, variant, biotype, serotype or genotype within that family.

For the invention "porcine" refers to animals of the family of Suidae, and preferably to animals of the genus Sus, for example: a wild or a domestic pig, wild boar, babirusa, or warthog. This also includes porcine indicated by an arbitrary name referring to their sex, age, or size, such as: sow, boar, hog, gilt, weaner, or piglet.

As used herein, the term "avian" refers to avians of agricultural relevance, such as: chicken, turkey, duck, goose, partridge, peacock, quail, pigeon, pheasant, guinea fowl, or ostrich. Preferably avian are chicken, turkey, duck, or goose. More preferably the avian are chicken or turkey. Most preferred the avian are chicken.

Avians can be of any type such as layers, breeders, broilers, combination breeds, or parental lines of any of such breeds. Preferred avian type is broilers.

As used herein the term "Tilapia" can include nearly a hundred species of bony fin fish from the Cichlidae family. Tilapia are mainly freshwater fish inhabiting shallow streams, ponds, rivers and lakes and less commonly found living in brackish water.

A "kit of parts" for the invention is typically a packaged combination of containers with specific compositions in predetermined amounts, which kit may include or refer to instructions for performing the preparation and vaccination of the invention.

The target for the vaccine, the method of immunizing, and the compounds and uses for protecting animals of the invention, are animals in need of a vaccination against infection or disease caused by the particular pathogen from which the encoded antigen originates. The age, weight, sex, immunological status, and other parameters of the target to be vaccinated/protected/immunized are not critical, although it is clearly favorable to vaccinate healthy, uninfected targets, and to vaccinate as early as possible.

As used herein, a "phylogenetic cluster" is a set of influenza virus neuraminidases that have been grouped together (on the same branch) in a phylogenetic tree or evolutionary tree that is rooted back to a similar (homologous) ancestor. For the IAV-S neuraminidases (NAs) found in the U.S., there are two predominant phylogenetic clusters of N1, N1-classic and N1-pandemic, and two predominant phylogenetic clusters of N2, N2-1998 and N2-2002. The N1 classic phylogenetic cluster contains the NAs grouped together with the NA from the H1N1 classic porcine influenza virus. The N1 pandemic phylogenetic cluster contains the NAs grouped together with the NA that comes from the H1N1 pandemic influenza virus. The N2-1998 phylogenetic cluster contains the NAs grouped together with the NA from the human H3N2 influenza virus that jumped into pigs in 1998, whereas the N2-2002 phylogenetic cluster contains the NAs grouped together with the NA from the human H3N2 influenza virus that jumped into pigs in 2002. [See, Anderson et al., *Influenza and other Respiratory Viruses* 7 (Suppl. 4): 42-51 (2013)].

The term "non-IAV-S", is used to modify terms such as pathogen, and/or antigen (or immunogen) to signify that the respective pathogen, and/or antigen (or immunogen) is neither an IAV-S pathogen nor an IAV-S antigen (or immunogen) and that a non-IAV-S protein antigen (or immunogen) does not originate from an IAV-S.

As used herein, a multivalent vaccine is a vaccine that comprises two or more different antigens, whereby the difference can be at anyone of a number of biological levels such as in genus, species, serotype, etc. In a particular embodiment of this type, the multivalent vaccine stimulates the immune system of the target animal against two or more different animal pathogens, or against immunologically distinct variants of the same pathogen.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient animal, e.g. a porcine.

The "administration" of the vaccine, respectively the components of the kit of the invention to an animal target can be performed using any feasible method and route. Typically the optimal way of administration will be determined by the type of the vaccine/compound applied, and the characteristics of the target and the disease that it is intended to protect against. Depending on how the vaccine/compound is formulated, different techniques of administration can be applied. For example as an O/W emulsion vaccine/compound of the invention can be administered by enteral or mucosal route, i.e. via eye drop, nose drop, oral, enteric, oro-nasal drop, spray. Other possibility is via a method of mass administration, such as via drinking water, coarse spray, atomization, on-feed, etcetera.

"Parenteral administration" includes subcutaneous injections, submucosal injections, intravenous injections, intramuscular injections, intradermal injections, and infusion.

"Mucosal administration" includes ocular, nasal, oral, oculo-nasal, intratracheal, intestinal, anal, and vaginal routes of administration.

"Topical administration" includes dermal and trans-dermal routes of administration.

The method, timing, and volume of the administration of a vaccine, respectively component of the kit of the invention, is preferably integrated into existing vaccination schedules of other vaccinations that the target animal may require, in order to reduce stress to the target and to reduce labor costs. These other immunizations themselves can be administered by a method of associated use, in a manner compatible with their registered application.

As used herein the term "antigenic fragment" in regard to a particular protein (e.g., a protein antigen) is a fragment of that protein that is antigenic, i.e., capable of specifically interacting with an antigen recognition molecule of the immune system, such as an immunoglobulin (antibody) or T cell antigen receptor. For example, an antigenic fragment of an IAV-S neuraminidase (NA) is a fragment of the NA protein that is antigenic. Preferably, an antigenic fragment of the present invention is immunodominant for antibody and/or T cell receptor recognition. In particular embodiments, an antigenic fragment with respect to a given protein antigen is a fragment of that protein that retains at least 25% of the antigenicity of the full length protein. In preferred embodiments an antigenic fragment retains at least 50% of the antigenicity of the full length protein. In more preferred embodiments, an antigenic fragment retains at least 75% of the antigenicity of the full length protein. Antigenic fragments can be as small as 12 amino acids or at the other extreme, be large fragments that are missing as little as a single amino acid from the full-length protein. In particular embodiments the antigenic fragment comprises 25 to 150 amino acid residues. In other embodiments, the antigenic fragment comprises 50 to 250 amino acid residues.

As used herein one amino acid sequence is 100% "identical" or has 100% "identity" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

As used herein, nucleotide and amino acid sequence percent identity can be determined using C, Mac Vector™ (Mac Vector, Inc. Cary, N.C. 27519), Vector NTI® (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG Package v. 7 (Genetics Computer Group, Madison, Wis.) Pileup program, using the default parameters.

When the alphavirus RNA replicon particles are stored separately, but intended to be mixed with other vaccine components prior to administration, the alphavirus RNA replicon particles can be stored in an aqueous stabilizing solution similar to that of the other components, e.g., a buffer, or a high sucrose solution.

A vaccine of the present invention can be readily administered by any standard "method of immunizing an animal". The skilled artisan will appreciate that the route of administration is chosen in consideration of the characteristics of the target animal and the vaccine to be administered. Preferably the vaccine composition is formulated appropriately for each type of target animal and route of administration.

For the invention, the "subunit of a micro-organisms" can be a biologic or synthetic molecule such as a protein, a carbohydrate, a lipopolysaccharide, a lipid, or a nucleic acid molecule.

It is well within reach of the skilled person to further optimize a vaccine, kit, method, or use of the invention. Generally this involves the fine-tuning of the efficacy of the vaccination/immunization to further improve its provided immune-protection. This can be done by adapting the dose, volume, adjuvant or antigen content of the administered material, or by administration via a different route, method, or regime. All these are within the scope of the invention.

It is also to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting, since the scope of the present invention will be limited only by the appended claims and equivalents thereof.

SEQUENCE TABLE

| SEQ ID NO: | Description (5' -> 3') | Type |
|---|---|---|
| 1 | ggcgcgccgcacc | nucleic acid |
| 2 | ttaattaa | nucleic acid |

The following non-limiting examples serve to provide further appreciation of the invention but are not meant in any way to restrict the effective scope of the invention.

EXAMPLES

Example 1

An Oil Adjuvant Improves Magnitude and Duration of Antibody Response in Swine to an Alphavirus RNA Replicon Particle Encoding a Porcine Influenza Virus Hemagglutinin

Materials and Methods

The VEE replicon vectors designed to express a hemagglutinin (HA) gene were constructed as previously described [see U.S. Pat. No. 9,441,247 B2; the contents of which are hereby incorporated herein by reference], with the following modifications: the HA gene insert was subjected to sequence optimization (ATUM, CA, USA). The TC-83-derived replicon vector "pVEK" [disclosed and described in U.S. Pat. No. 9,441,247 B2] was digested with restriction enzymes AscI and PacI. A DNA plasmid containing the codon-optimized open reading frame sequence of the N1 or N2 genes with 5' flanking sequence (5'-GGCGCGCCGCACC-3') [SEQ ID NO: 1] and 3' flanking sequence (5'-TTAATTAA-3') [SEQ ID NO: 2], was similarly digested with restriction enzymes AscI and PacI. The synthetic gene cassette was then ligated into the digested pVEK vector, and the resulting clones were re-named "pVHV-N1-pandemic", "pVHV-N1-classic", pVHV-N2-2002", and "pVHV-N2-1998". The "pVHV" vector nomenclature was chosen to refer to pVEK-derived replicon vectors containing transgene cassettes cloned via the AscI and PacI sites in the multiple cloning site of pVEK.

Production of TC-83 RNA replicon particles was conducted according to methods previously described [U.S. Pat. No. 9,441,247 B2 and U.S. Pat. No. 8,460,913 B2; the contents of which are hereby incorporated herein by reference]. Briefly: pVHV replicon vector DNA and helper DNA plasmids were linearized with NotI restriction enzyme prior to in vitro transcription using MegaScript™ T7 RNA polymerase and cap analog (Promega, Madison, Wis.). Importantly, the helper RNAs used in the production lack the VEE subgenomic promoter sequence, as previously described [Kamrud et al., *J Gen Virol.* 91(Pt 7): 1723-1727 (2010)]. Purified RNAs for the replicon and helper components were combined and mixed with a suspension of Vero cells, electroporated in 4 mm cuvettes, and returned to OptiPro™ SFM cell culture media (Thermo Fisher, Waltham, Mass.). Following overnight incubation, alphavirus RNA replicon particles were purified, formulated in phosphate buffered saline with 5% w/v sucrose and 1% v/v porcine serum, sterilized by passing through a 0.22 micron membrane filter, and dispensed into aliquots for storage. Titer of functional RP was determined by infection-immunofluorescence assay on Vero cell monolayers. Batches of RP were identified according to the antigen encoded by the packaged replicon.

Ten piglets negative for antibodies to porcine influenza virus were randomized into groups of five pigs. An RP vaccine expressing the hemagglutinin antigen of an H3N2 porcine influenza strain was prepared at a titer of 5x105 RP/dose. Immediately prior to vaccination, the RP-only group's vaccine was diluted 1:1 (v/v) with sterile PBS diluent, while the RP+adjuvant group's vaccine was diluted 1:1 (v/v) with XSolve™ adjuvant. Pigs were then vaccinated intramuscularly with 2.0 mL of the appropriate material. The vaccination process was conducted on study days 0 and 21, each time with a fresh preparation of vaccine. Sera collected during the trial were assayed for hemagglutination inhibition (HI) activity using H3N2 porcine influenza virus antigen. The results were reported as the highest dilution with inhibitory activity; titers of less than 1:10 were reported as 1:9; titers of >640 were reported as 1:641. Geometric mean titers are shown in Table 1.

TABLE 1

Geometric Mean Hemagglutination Inhibition (HI) Titer

| | Study Day | | | | | | |
|---|---|---|---|---|---|---|---|
| | 0 | 21 | 28 | 35 | 56 | 70 | 84 |
| RP | 9.0 | 9.0 | 25.8 | 22.5 | 12.9 | 9.4 | 9.4 |
| RP + Adjuvant | 9.0 | 9.2 | 242.7 | 211.1 | 91.9 | 52.8 | 52.8 |

At the relatively low dose of 5×10^5 RP, the non-adjuvanted vaccine induced a low-magnitude, brief and transient HI titer. By comparison, the adjuvanted vaccine induced high HI titers after the booster vaccination, and those HI titers remained elevated till the end of the 84-day trial.

This finding was the first clear indication that XSolve™ could have such a dramatic effect on porcine RP immunization at very low doses (5×10/\5 RP). Prior studies using RP vaccine without adjuvant, had to employ much higher amounts of the RP component per dose, e.g.: 1×10/\9 for FMD RP, and 5×10/\7 for SIV RP).

Example 2

An Oil Adjuvant Improves Magnitude and Duration of Antibody Response in Swine to a Multivalent Alphavirus RNA Replicon Particle Encoding Porcine Influenza Virus Antigens Groups of weaned piglets from a herd negative for porcine influenza were randomized into treatment groups as indicated in Table 2. A multivalent alphavirus RNA replicon particle vaccine for porcine influenza was blended using eight individual RNA Particle antigens expressing either HA or NA from various strains of porcine influenza, each blended to approximately 1×10^7 RP/dose. Two H3, four H1, one N1, and one N2 antigen were included, and a paired serological assay (HI or NI) was used to assess antibody response to each antigen. The study was run as a duplicated design, with half of the animals challenged with an H1N1 virus, and the other half challenged with an H1N2 virus.

TABLE 2

Experimental Protocol of Example 2

| Group | Number of pigs | Vaccine | Challenge Strain |
|---|---|---|---|
| 1 | 16 | multivalent RP-only | H1N1 |
| 2 | 16 | multivalent RP + oil adjuvant | |
| 3 | 16 | Placebo | |
| 4 | 16 | multivalent RP-only | H1N2 |
| 5 | 16 | multivalent RP + oil adjuvant | |
| 6 | 16 | Placebo | |

Figure 1A:
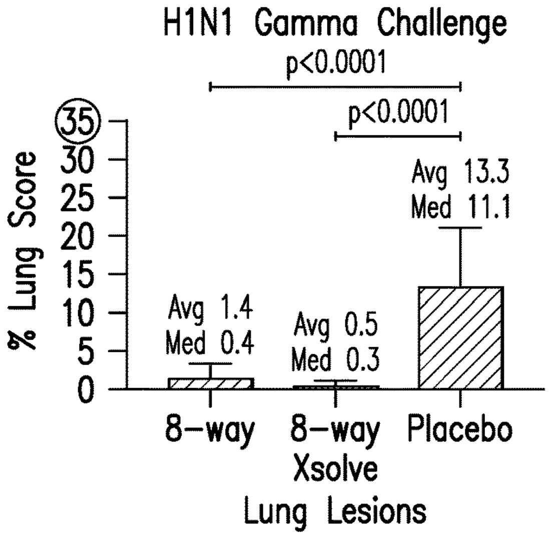
FIGS. 1A-1F and 2A-2F: Results from Example 2.
Figure 1B:
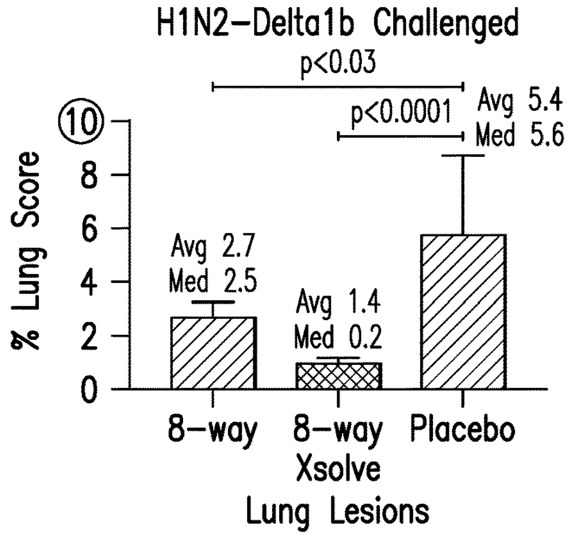
Figure 1C:
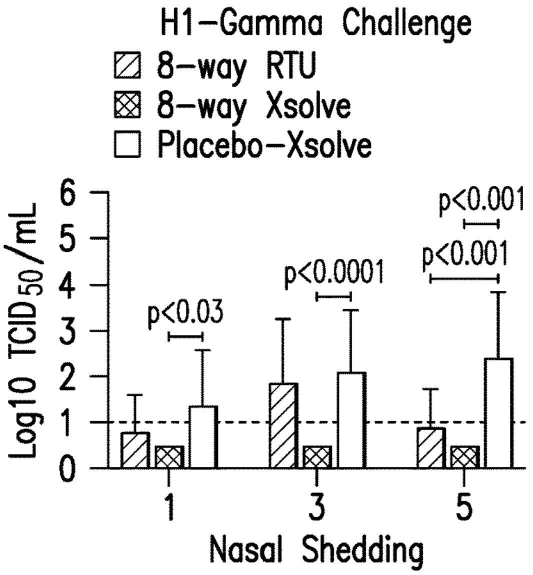
Figure 1D:
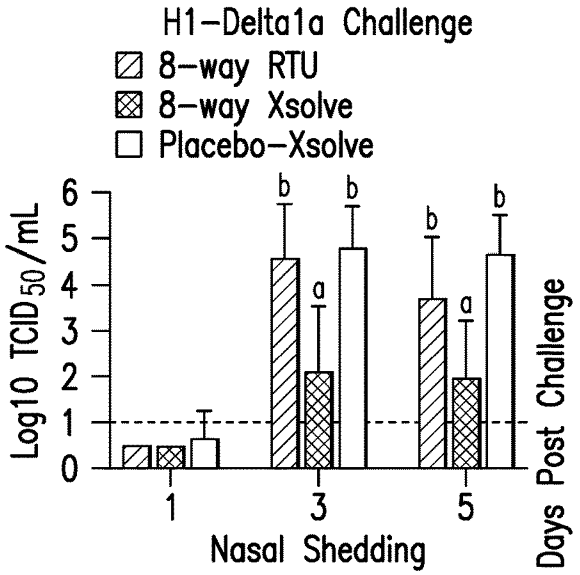
Figure 1E:
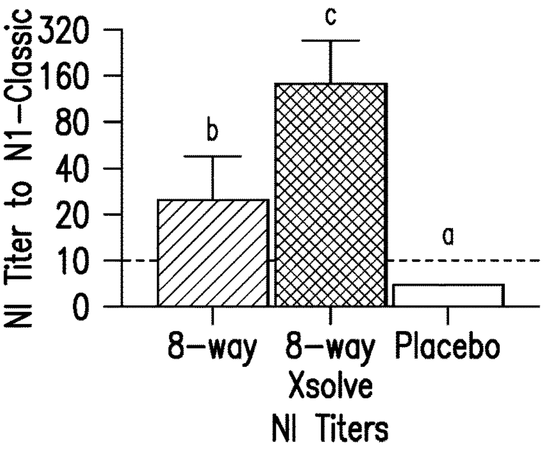
Figure 1F:
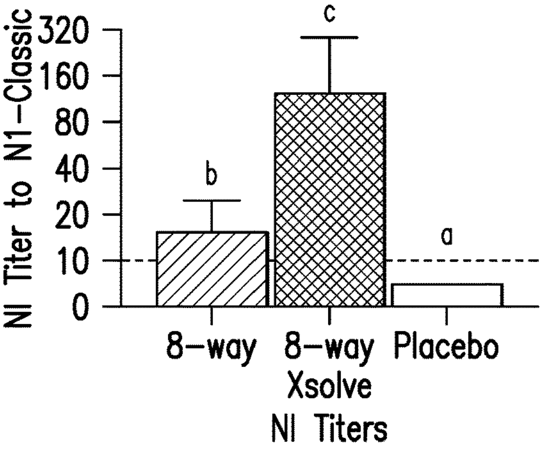
Figures 2A, 2B, 2C, 2D, 2E, 2F:
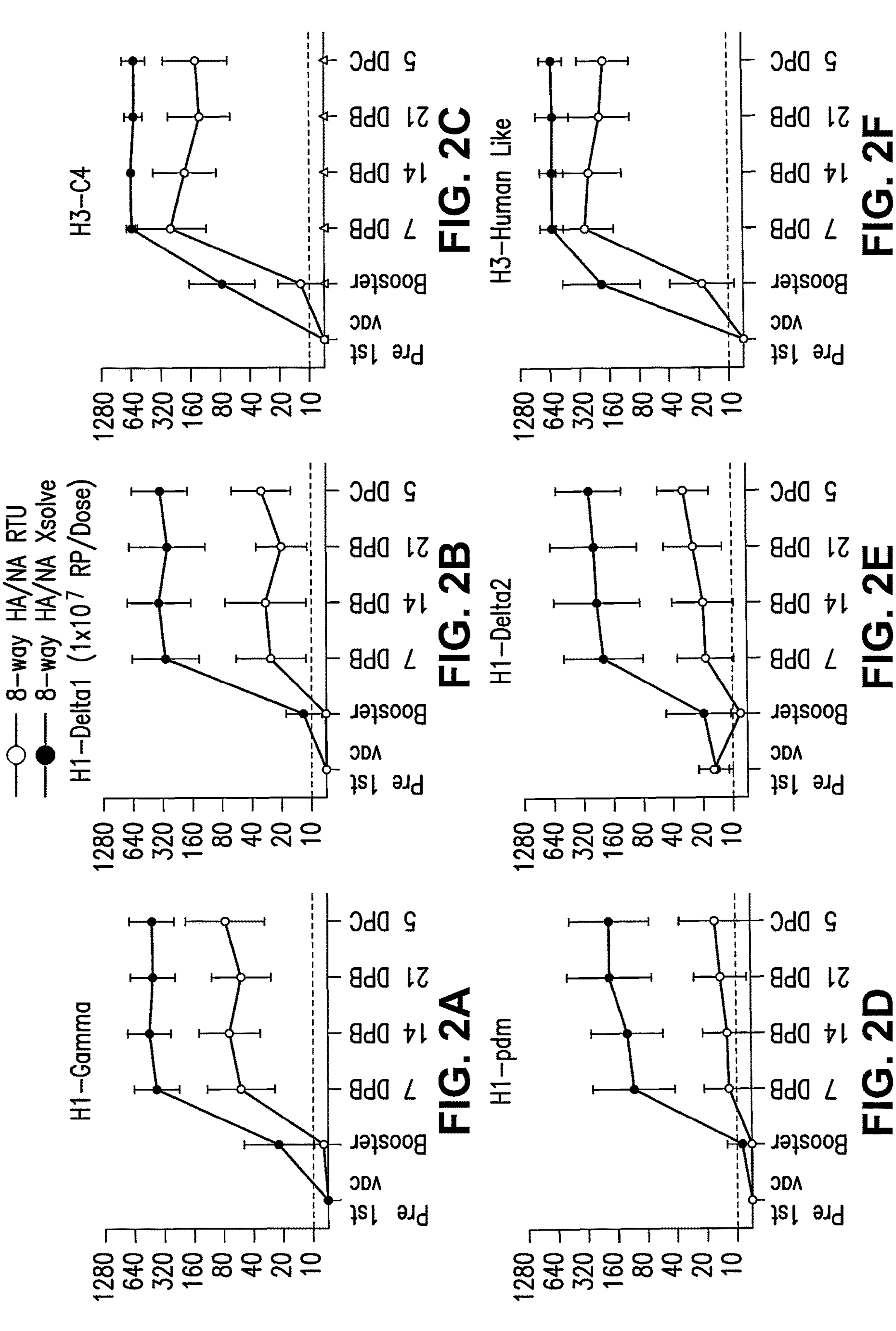

The use of XSolve™ oil adjuvant was found to significantly increase the magnitude of serological response for all eight vaccine fractions. While both vaccine formulations protected against lung lesions (FIGS. 1A-1B), however addition of XSolve™ improved the efficacy of the vaccine when measured by nasal shedding of H1N1 and H1N2 influenza virus (FIGS. 1C-1D). FIGS. 1E-1F represent the corresponding NI titer scores. The effect of the adjuvant on the HI titers is represented in FIGS. 2A-2F.

This study demonstrated that non-adjuvanted multivalent SIV RP induced antibodies to all fractions, but that addition of an oil adjuvant significantly boosted the immune response of all fractions. The reduction of nasal shedding and the tighter clustering of lung scores, represent important clinical advantages, e.g. in regard to the limitation of horizontal spread of an infection in a herd or population.

Example 3

Efficacy of an Adjuvanted Four-Way NA-RP Vaccine Against H1N1 Infection in Weaned Pigs, Having N1 Antibodies at the Time of First Vaccination A vaccination-challenge study was undertaken to determine the efficacy and immunogenicity of two dose levels of an adjuvanted four-way NA-RP vaccine. The adjuvanted vaccine included four RP constructs, each of which individually encoded a single, different NA gene of a contemporary U.S. IAV-S isolate. Together these NA genes represent two N1 phylogenetic clusters (N1-classic and N1-pandemic) and two N2 clusters (N2-1998 and N2-2002) (see Table 3). The adjuvanted vaccine was administered by two intramuscular (IM) vaccinations at 1 mL/dose, in weaned pigs antibody-positive to N1-classic antigen at the time of their first vaccination. The efficacy of the adjuvanted four-way NA-RP vaccine was tested against a heterologous N1 (H1N1 virus) challenge infection.

Materials and Methods

Construction of NA-RP Antigens:

The replication defective alphavirus RNA replicon particles (RPs) encoded the neuraminidase (NA) gene, and were prepared essentially as described in Example 1 herein.

TABLE 3

N1 and N2 Genes Encoded in NA-RP Constructs of Example 3

| NA phylogenetic cluster | Gene donor strain | GenBank Accession no. |
|---|---|---|
| N1-classic | A/porcine/Iowa/A01410307/2014 (H1N1) | KJ605083 |
| N1-pandemic | A/porcine/Minnesota/A01483170/2014 (H1N1) | KP036969 |
| N2-1998 | A/porcine/Michigan/A02077465/2015 (H1N2) | KR982634 |
| N2-2002 | A/porcine/Illinois/A01475495/2014 (H1N2) | KJ941362 |

n = 10 pigs per group

Viruses

The challenge viruses were obtained from USDA National Veterinary Services Laboratories.

A/porcine/Illinois/A01554351/2015 (H1N1) possesses an HA gene of the H1-gamma cluster and an NA gene of the N1-classic cluster. The viruses were propagated in an MDCK cell culture. Confluent cells were infected for approximately 48 hours, until cytopathic effect was evident in over 70% of the cell monolayer. At harvest, the supernatant was removed from vessels and clarified by centrifugation before frozen storage of the virus.

Animals

The weaned piglets were selected from a high health herd based on serology screening to confirm the lack of preexisting HI or NI (neuraminidase inhibition) antibodies to the vaccine and challenge strains. The animals were a mix of male and female, and were approximately three weeks of age at the time of first vaccination.

Vaccination and Challenge

The treatment groups are outlined in Table 4. A Four-way NA-RP vaccine was formulated at 10/\6 copies each RP/dose, based on an immunofluorescence-based potency assay to quantitate functional RPs. NA-RP antigens were formulated in a stabilizer consisting of 1% porcine serum and 5% sucrose. The placebo vaccine consisted of the same stabilizer but without the antigen. Vaccines were mixed with XSolve™ oil adjuvant (1:1 v/v, 1 mL dose), shortly prior to administration via IM route to pigs at 3 and 7 weeks of age. Dose levels were back-titrated by IFA test on retained vaccine material following vaccination. Serum samples were collected on the day of the first vaccination, the day of second vaccination, and the day of challenge infection.

At one day prior to the first vaccination all pigs were weighed, and pigs in the N1-classic antibody positive groups were injected subcutaneously with a 2 mL/kg dose of N1-classic hyperimmune serum (anti-NI antibody-titer of 1:2560 to N1-classic antigen).

TABLE 4

Treatment Groups with H1N1 Challenge Strain as in Example 3

| Group | N1-Classic Antibody Status | Vaccine (+XSolve ™) | RPs per 1 mL Dose |
|---|---|---|---|
| 1 | Positive | 4-way NA-RP | 10^6 |
| 2 | Negative | 4-way NA-RP | 10^6 |
| 3 | Positive | Placebo | — |
| 4 | Negative | Placebo | — |

(n = 10 pigs per group)

The challenge infection was administered to pigs at 3 weeks after the second vaccination. Challenge materials of the H1N1 (H1-gamma-N1-classic) were formulated to the target dose of 10^6.5 TCID50/pig (6 mL volume). The challenge material was administered by the intratracheal route. The challenge virus doses were confirmed by back-titration of retained challenge material. Nasal swabs were collected from all pigs at −1, 1, 3, and 5 days post challenge.

Necropsy was performed at 5 days post challenge. Pigs were euthanized by barbiturate overdose at 5 DPC under the supervision of a licensed veterinarian. Lungs were collected and observed in order to document the surface area of each lobe affected by macroscopic lesions, resulting in a comprehensive percent lung lesion score. Bronchoalveolar lavage and nasal swabs were collected from all pigs to measure virus titers. Lung sections were collected for histopathologic analysis of microscopic lesion.

Immune Response Analysis:

IAV-S specific antibodies in pig serum samples were determined by NI test. Sera were heat inactivated for 30-60 minutes at 56° C. The NI test was performed with minor modifications to the method of Sandbulte & Eichelberger (*Methods Mol Biol* 1161: 337-45, 2014). Briefly, 2-fold serial dilutions of serum were mixed with the expressed protein antigen at equal volumes on fetuin-coated 96-well plates and incubated overnight at 37° C. Peanut agglutinin horseradish peroxidase conjugate was added for 2 hours at room temperature to bind fetuin molecules stripped of sialic acid. Signal was obtained with TMB coloring substrate, and results were read at 650 nm. The mean optical density (OD) of the negative control, which lacked NA antigen, was subtracted from all wells. Then the OD values of test samples were normalized on a scale of 0-100%, where the mean OD of positive control wells (containing NA antigen, but no serum) was defined as 100%. The NI antibody titer was defined as the highest dilution of the sample that inhibited ≥50% of neuraminidase activity.

Pathological Examination of Lungs

Macroscopic lesions observed on the exterior of all lung lobes (well-demarcated purple to plum-colored consolidations) were recorded on grid diagrams of lung anterior and posterior. Comprehensive scores (percent lung lesion) for each pig were calculated according to the number of lesion-affected grids.

Virus Shedding

Nasal swabs and BAL fluids were 10-fold serially diluted with infecting media [Dulbeco's minimum essential medium (DMEM) supplemented with 0.3% bovine serum albumin, fraction V; 2 mM L-Glutamine; 25 µg/mL Gentamycin; 2 µg/mL trypsin IX], and 100 µL of each dilution was added to quadruplicate wells of confluent MDCK cells in a 96-well plate. The plates were incubated at 37° C. with 5% $CO_2$ and observed after 72 hours for the presence of infectious virus by hemagglutination tests of supernatants from each well. IAV-S titers were calculated by the method of Spearman-Karber and expressed as Log 10 TCID50 per mL.

Results

Figure 3:
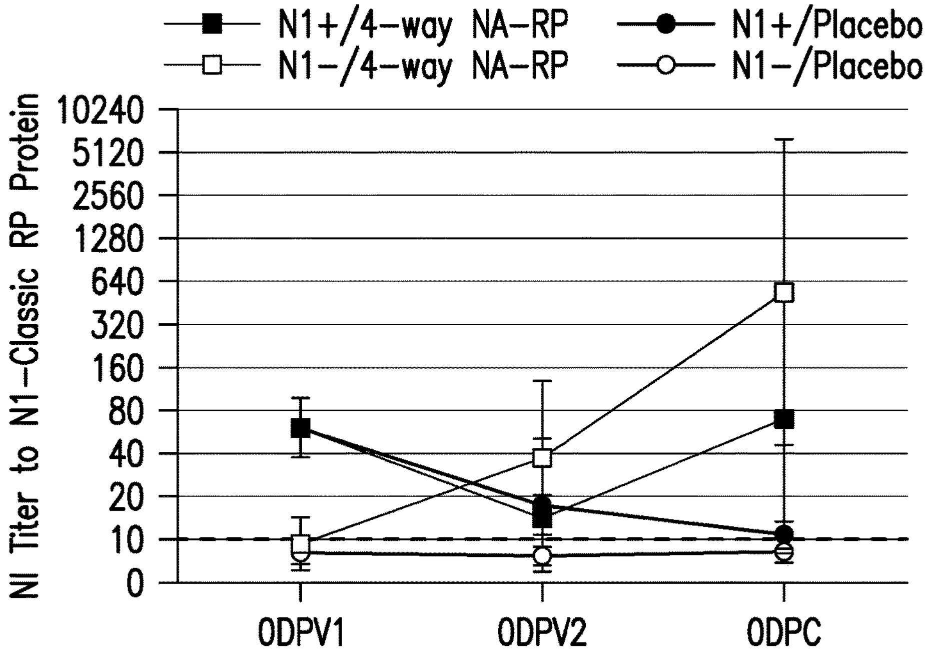
FIG. 3: Serum antibody responses to N1-classic antigen in pigs vaccinated with multivalent NA-RP of Example 3.

Immune responses of pigs vaccinated with multivalent NA-RP are represented in FIG. 3. Noteworthy is that:

The pigs passively transferred with N1-classic hyperimmune serum at one day prior to receiving their first vaccination had N1-classic antibody titers of 40-80 at the time of vaccination.

After two vaccinations of the 4-way NA-RP vaccine with XSolve™ adjuvant both the seronegative and the N1-antibody seropositive pigs showed a significant increase of their N1-classic antibody titers. This indicated that RP vaccination with oil adjuvant was effective even in target animals positive for antibodies against the RP-encoded antigen.

The NI titer of pigs in the N1-classic negative/placebo vaccinated group remained seronegative.

The Efficacy of 4-way NA-RP vaccine against challenge infections, in respect of Lung Lesions is represented in FIG. 4. Noteworthy is that the 4-way NA-RP vaccination was highly efficacious in reducing lung lesions both when vaccinating pigs with- or without N1-classic antibody at the time of their first vaccination. In both groups the percent lung lesions was significantly reduced compared to both placebo vaccinated groups.

Example 4

An Oil Adjuvant Improves Magnitude of Antibody Response Inswine to an Alphavirus RNA Replicon Particle Encoding Porcine Epidemic Diarrhea Virus Antigen, Relative to an Aluminum Adjuvant or Water Nine piglets, approximately three weeks of age, were randomized into groups of three animals each. An alphavirus RNA replicon particle vaccine expressing the Spike glycoprotein of porcine epidemic diarrhea virus (PEDV) was prepared and lyophilized in 20-dose vials. On study day 0, pigs were vaccinated intramuscularly with 1.0 ml of the alphavirus RNA replicon particle vaccine that had been rehydrated with either water, aluminum hydroxide adjuvant, or XSolve™ adjuvant. On study day 21, the process was repeated with fresh vials of vaccine. The final titer of alphavirus RNA replicon particle per dose after rehydration was determined by immunofluorescence assay, and was approximately 7×10/\6 RP/dose for all groups. Sera collected during the trial were assayed for PEDV-neutralizing antibodies, see Table 5.

TABLE 5

The Effect of Different Adjuvants on the Development of Neutralizing Antibodies

| Adjuvant | Pig # | Titer of PEDV neutralizing Ab<br>Prebleed | 20 DPV | 6 DPV2 | 13 DPV2 | 20 DPV2 |
|---|---|---|---|---|---|---|
| no adjuvant | 154 | <20 | <20 | 20 | 40 | 20 |
| | 157 | 20 | <20 | <20 | 20 | <20 |
| | 158 | <20 | <20 | <20 | <20 | <20 |
| XSolve ™ | 151 | <20 | <20 | 160 | 320 | 160 |
| | 155 | <20 | <20 | 40 | 80 | 20 |
| | 159 | <20 | <20 | 160 | 160 | 160 |
| Alhydrogel ® | 152 | <20 | <20 | <20 | <20 | 20 |
| | 153 | 20 | <20 | <20 | <20 | 40 |
| | 156 | <20 | 20 | <20 | <20 | 40 |

Pigs treated with non-adjuvanted vaccine had low or undetectable neutralizing antibodies after two doses of vaccine. All pigs treated with aluminum hydroxide-adjuvanted vaccine developed neutralizing antibodies that were just above the detection limit. In contrast, the XSolve™-adjuvanted vaccine induced higher neutralizing antibodies after two doses of vaccine, and all three pigs reached a minimum antibody titer higher than the peak titer observed in the other test groups. The use of Aluminium-hydroxide as adjuvant was thus ineffective, and was substantially outperformed by the oil adjuvant.

Example 5

An Oil Adjuvant Improves Vaccination Efficacy in Chickens of an Alphavirus RNA Replicon Particle Encoding an Influenza Antigen Day-old chicks were randomized into groups of ten birds. An alphavirus RNA replicon particle vaccine expressing the hemagglutinin antigen of an H3N2 swine influenza strain was prepared at a titer of 1×10/\8 RP/dose. Immediately prior to vaccination, the vaccine for the group receiving RP only, was diluted 1:1 (v/v) with sterile PBS diluent, while the alphavirus RNA replicon particle plus adjuvant group's vaccine was diluted 1:1 (v/v) with XSolve™ adjuvant. Sera from chicks were assayed for hemagglutination inhibition (HI) titer on study days 0, 7, and 14 post vaccination.

TABLE 6

The Effect of Oil Adjuvant on HI titer

| Vaccine | Number of birds | Geometric mean HI titer<br>Day 0 | Day 7 | Day 14 |
|---|---|---|---|---|
| RP-only | 10 | 25 | 25 | 18 |
| RP + oil adjuvant | 10 | 25 | 35 | 55 |
| Placebo | 10 | 25 | 27 | 14 |

The addition of XSolve™ adjuvant to the alphavirus RNA replicon particle vaccine induced a clear increase to the bird's HI titers after a single vaccination, in contrast to non-adjuvanted and to placebo vaccines.

Example 6

An Oil Adjuvant Improves the Efficacy in Chickens of an Alphavirus RNA Replicon Particle Vaccine Expressing an IBDV Antigen This vaccination-challenge experiment tested the effect of an oil adjuvant on the vaccination-efficacy of an RP expressing the VP2-4-3 polyprotein antigen from Infectious Bursal Disease virus (IBDV) of strain Faragher 52/70. Test animals were SPF (specific pathogen free) chickens that were negative for antibody against IBDV. Group size was 5 or 10 birds. Vaccination was done by subcutaneous route at day-of-age (day-of-hatch); one group (n=5) was mock vaccinated with phosphate-buffered saline (PBS). One vaccinated group received the RP vaccine in aqueous buffer, the other vaccine group received RP vaccine mixed 1:1 with XSolve™ adjuvant. At 28 days post vaccination, all groups were given a challenge infection with virulent IBDV strain CS89, by eyedrop route. The vaccination efficacy was monitored by necropsy performed 10 days postchallenge, scoring Bursal tissues for gross lesions, and by histopathology, according to well-known criteria for IBDV infection.

TABLE 7

The effect of oil adjuvant on RP vaccination-efficacy against severe IBDV challenge

| Group | Vaccine | Number of birds | % Protection: Based on Gross Bursal Lesions | % Protection: Based on Microscopic Lesions |
|---|---|---|---|---|
| 1 | RP-IBDV Polyprotein | 10 | 0% | 0% |
| 2 | RP-IBDV Polyprotein + XSolve ™ | 10 | 100% | 100% |
| 3 | Placebo | 5 | 0% | 0% |

Evidently, the addition of oil-adjuvant to the RP vaccine had a dramatic positive effect on the vaccination efficacy against a severe challenge infection: improving the chicken's immune response from zero to fully protective.

Example 7

An Oil Adjuvant Also Improves Efficacy of an Alphavirus RNA Replicon Particle Vaccine in Fish An alphavirus RNA replicon particle vaccine expressing the major capsid protein of red sea bream iridovirus (RSIV) was prepared by standard methods as described herein. Tilapia were vaccinated intramuscularly with 0.05 ml vaccine, and then challenged at different times post-vaccination. Thirty fish per treatment and per challenge time were used in the study. The alphavirus RNA replicon particle vaccines were mixed 1:1 (v/v) with PBS, or with SVEA™, the dual non-mineral oil adjuvant, shortly before vaccination. The titer of RP per treatment was 1×10/\7 RP/dose. Control fish were vaccinated with a placebo vaccine.

TABLE 8A

The Effect of Oil Adjuvant on Percent Survival of Tilapia

| Vaccine treatment group | Survival percentage at 14 days post-challenge: 3-week low-dose challenge | 3-week high-dose challenge | 6-week low-dose challenge | 6-week high-dose challenge |
|---|---|---|---|---|
| RP-Irido without adjuvant | 77% | 47% | 83% | 47% |
| RP-Irido with oil adjuvant | 90% | 43% | 83% | 70% |
| Non-vaccinated control | 43% | 27% | 67% | 37% |

TABLE 8B

The Effect of Oil Adjuvant on Relative Percent Survival of Tilapia

| Vaccine treatment group | Relative percent survival versus controls: 3-week low-dose challenge | 3-week high-dose challenge | 6-week low-dose challenge | 6-week high-dose challenge |
|---|---|---|---|---|
| RP-Irido without adjuvant | 58.8 | 27.3 | 50.0 | 15.8 |
| RP-Irido with oil adjuvant | 82.4 | 22.7 | 50.0 | 52.6 |
| Non-vaccinated control | n/a | n/a | n/a | n/a |

At both the "three-week low-dose" and "six-week high-dose" challenges, the adjuvant strongly improved the relative survival of RP-vaccinated fish. The two other challenge treatments yielded equivalent results. The alphavirus RNA RP vaccine with adjuvant was thus considerably more effective compared to the RP vaccine without adjuvant, and provided efficacious vaccination even with only a single dose vaccination.

Example 8

Efficacy of Simultaneous and of Concurrent Use of RP and Oil Adjuvant

An experiment was performed in swine, using the 4-way swine influenza virus NA vaccine of alphavirus RNA replicon particles, as described in Example 3. This served to illustrate the efficacy of the different types of use of the vaccine components: RP and oil adjuvant.

Materials and Methods

Pigs were vaccinated at approximately 4 and 7 weeks of age. The four-way NA vaccine was a mixture of the dual-gene N1, and dual-gene N2 RP constructs, as described in Example 3, each administered at approximately 2×10/\6 RP/dose. All groups contained 4 pigs. The layout of the test protocol is presented in Table 9. Group 2 received the NA RPs mixed with XSolve™ adjuvant, in simultaneous use.

Groups 3 and 4 tested the effect of concurrent use of the RP and the oil adjuvant: administrations were given within about 10 minutes of each other, and at either the same side of the neck (>5 cm apart), or at opposite sides of the neck.

One control group, group 5, was included using an RP encoding a swine influenza HA H1 antigen. This was administered at about 1×10^7 RP/dose.

Sera were collected at the day of 1st vaccination, the day of second vaccination, and at 7 days post-second vaccination. These sera were tested on separate homologous NI assays for each of the 4 NA types.

The resulting NI titers measured are presented in FIGS. 5 and 6, whereby FIG. 5 presents the NI titers against the N1 classic NA antigen at the three time points measured over time, including the standard deviations. FIG. 6 represents the group mean NI titers of the combined 4 NA types, at 7 days post second vaccination.

TABLE 9

Experimental Protocol of Example 8

| Group | RP | Adjuvant | Administration |
|---|---|---|---|
| 1 | SIV 4-way NA | None | Inject IM, 1 ml dose |
| 2 | | Xsolve ™ | Mix and inject IM, 1 ml dose |
| 3 | | | Inject RP and oil adjuvant separately: 0.5 ml each, IM, same side of neck |
| 4 | | | Inject RP and adjuvant separately: 0.5 ml each, IM, opposite sides of neck |
| 5 | SIV HA H1 | None | Mix and inject IM, 1 ml dose |

Results and Conclusions

From the results measured in Example 8, several effects could be observed:

The patterns of NI titers for the 4 NA types at the three time points measured, were almost identical, therefore the results presented in FIG. 5 of NA N1 classic are indicative of the titer-patterns against the other 3 NA types.

Also, the patterns of NI titer response for the 4 NA types at 7 dpv2, as presented in FIG. 6 are largely the same.

The NI titer results of the HA H1 RP control (group 5) as expected did not induce an NI titer; this sets the titer threshold for a specific response.

Except for some experimental variation, most of the NI titers in the groups 2-4, receiving RP and oil adjuvant, were significantly higher than those of the group receiving only RPs (group 1). This illustrates that oil adjuvant strongly boosts the immunization by RPs.

The group receiving RP and oil adjuvant in simultaneous use (group 2), confirmed the strong effect of the oil adjuvant already observed in previous Examples.

The immunizing effect of the concurrent use of RP and of oil adjuvant (groups 3-4) came very close to that of the simultaneous use: a strong stimulation of RP immune response. There was no clear effect of a difference in the site of administration.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

We claim:

1. A vaccine comprising an alphavirus RNA replicon particle encoding an antigen originating from an animal pathogen, wherein the vaccine also comprises an oil adjuvant which comprises a mineral oil and a non-mineral oil, wherein the mineral oil is a liquid paraffin oil and wherein the non-mineral oil is Vitamin E acetate.

2. The vaccine of claim 1, wherein the amount of the mineral oil in the oil adjuvant is 1-70% v/v of the oil adjuvant.

3. The vaccine of claim 1, wherein the total amount of the non-mineral oil in the oil adjuvant is 0.1-30% w/v of the oil adjuvant.

4. The vaccine of claim 2, wherein the oil adjuvant is formulated as an oil-in-water emulsion.

5. The vaccine of claim 1, wherein the alphavirus RNA replicon particle is a Venezuelan Equine Encephalitis (VEE) alphavirus RNA replicon particle.

6. The vaccine of claim 5, wherein the encoded antigen originating from an animal pathogen is an antigen originating from a pathogen of an animal selected from the group consisting of a fish, an avian, and a mammal.

7. The vaccine of claim 6, wherein the mammal is a porcine.

8. The vaccine of claim 6, wherein the avian is a chicken or a turkey.

9. The vaccine of claim 6, wherein the fish is a member of the Cichlidae family.

10. A kit comprising at least two containers, wherein at least one container comprises an alphavirus RNA replicon particle encoding an antigen originating from an animal pathogen, and at least one container comprises an oil adjuvant, which comprises a mineral oil and a non-mineral oil; wherein the mineral oil is a liquid paraffin oil and wherein the non-mineral oil is Vitamin E acetate.

11. A method of immunizing an animal comprising administering to the animal immunologically effective amounts of the vaccine of claim 1.

12. The method of claim 11, wherein the animal is a fish and the encoded antigen originating from an animal pathogen is an antigen originating from a fish pathogen.

13. The method of claim 11, wherein the animal is a mammal and the encoded antigen originating from an animal pathogen is an antigen originating from a pathogen of a mammal.

14. The method of claim 13, wherein the mammal is a porcine and the antigen originating from a pathogen of a mammal is an antigen originating from a pathogen of porcine.

15. The method of claim 11, wherein the alphavirus RNA replicon particle and the oil adjuvant are administered in or on the target animal body in simultaneous use or in concurrent use.

16. A method of making the vaccine of claim 1 comprising the step of admixing the alphavirus RNA replicon particle encoding an antigen originating from an animal pathogen, and the oil adjuvant.

17. The method of claim 16, wherein the alphavirus RNA replicon particle is comprised in an aqueous solution.

18. The method of claim 17, wherein the volume ratio (v/v) of the aqueous solution and the oil adjuvant is between 1:2 to 2:1.

19. The method of claim 17, wherein the volume ratio (v/v) of the aqueous solution and the oil adjuvant is about 1:1.

* * * * *